US011364272B2

(12) United States Patent
Yun et al.

(10) Patent No.: US 11,364,272 B2
(45) Date of Patent: Jun. 21, 2022

(54) ANTICANCER COMPOSITION COMPRISING TUMOR-SPECIFIC ONCOLYTIC ADENOVIRUS AND IMMUNE CHECKPOINT INHIBITOR

(71) Applicant: Genemedicine CO., LTD., Seoul (KR)

(72) Inventors: Chae Ok Yun, Seoul (KR); Hyo Min Ahn, Incheon (KR)

(73) Assignee: GENEMEDICINE CO., LTD., Seoul (KR)

( * ) Notice: Subject to any disclaimer, the term of this patent is extended or adjusted under 35 U.S.C. 154(b) by 320 days.

(21) Appl. No.: 16/553,275

(22) Filed: Aug. 28, 2019

(65) Prior Publication Data

US 2019/0388488 A1 Dec. 26, 2019

Related U.S. Application Data

(63) Continuation of application No. PCT/KR2018/002439, filed on Feb. 28, 2018.

(30) Foreign Application Priority Data

Feb. 28, 2017 (KR) .................. 10-2017-0026339

(51) Int. Cl.
| | | |
|---|---|---|
| A61K 35/761 | (2015.01) | |
| A61P 35/00 | (2006.01) | |
| A61K 38/19 | (2006.01) | |
| A61K 38/20 | (2006.01) | |
| A61K 38/22 | (2006.01) | |
| A61K 45/06 | (2006.01) | |

(52) U.S. Cl.
CPC .......... *A61K 35/761* (2013.01); *A61K 38/193* (2013.01); *A61K 38/208* (2013.01); *A61K 38/2221* (2013.01); *A61P 35/00* (2018.01); *A61K 45/06* (2013.01)

(58) Field of Classification Search
CPC .................................................. A61K 35/761
See application file for complete search history.

(56) References Cited

U.S. PATENT DOCUMENTS 9,492,482 B2 11/2016 Beech et al.
2015/0118287 A1 4/2015 Hammond et al.

FOREIGN PATENT DOCUMENTS

| CA | 3046961 | | 6/2018 | | |
|---|---|---|---|---|---|
| KR | 10-2006-0045056 | | 5/2006 | | |
| KR | 10-2012-0010697 | * | 2/2012 | ............. | C12N 15/87 |
| KR | 10-2006-0045056 | * | 5/2016 | ............. | C12N 15/87 |
| RU | 2573912 | | 1/2016 | | |
| RU | 2014137169 | | 10/2016 | | |
| WO | WO 2013/123094 | | 8/2013 | | |
| WO | WO 2015/153417 | | 10/2015 | | |
| WO | WO 2016/008976 | | 1/2016 | | |

OTHER PUBLICATIONS

Rojas et al. (Clinical Cancer Re3search [2015]; 21(24): 5543-5551). (Year: 2015).*
Notice of Reason for Rejection dated Aug. 3, 2020 From the Japan Patent Office Re. Application No. 2019-547084. (3 Pages).
Requisition by the Examiner dated Jul. 21, 2020 From the Innovation, Science and Economic Development Canada, Canadian Intellectual Property Office Re. Application No. 3,054,664. (6 Pages).
Choi et al. "Evolution of Oncolytic Adenovirus for Cancer Treatment", Advanced Drug Delivery Reviews. 64(8): 720-729, Available Online Dec. 24, 2011.
Du et al. "Tumor-Specific Oncolytic Adenoviruses Expressing Granulocyte Macrophage Colony-Stimulating Factor or Anti-CTLA4 Antibody for the Treatment of Cancers", Cancer Gene Therapy, 21(8): 340-348, Published Online Jul. 18, 2014.
Huang et al. "Combining Antiangiogenic Therapy With Immunotherapy Exerts Better Therapeutical Effects on Large Tumors in a Woodchuck Hepatoma Model", Proc. Natl. Acad. Set. USA, PNAS, 107(33): 14769-14774, Published Online Aug. 2, 2010.
Huang et al. "Showing the Way: Oncolytic Adenoviruses as Chaperones of Immunostimulatory Adjuncts", Biomedicines, 4(3): 23-1-23-14, Published Online Sep. 19, 2016.
Quetglas et al. "Virotherapy With a Semliki Forest Virus-Based Vector Encoding IL12 Synergizes With PD-1/PD-L1 Blockade", Cancer Immunology Research, 3(5): 499-459, Published Online Feb. 17, 2015.
Supplementary European Search Report and the European Search Opinion dated Dec. 7, 2020 From the European Patent Office Re. Application No. 18761929.1.
Fukuhara et al. "Oncolytic Virus Therapy: A New Era of Cancer Treatment at Dawn", Cancer Science, XP055461452, 107(10): 1373-1379, Published Online Sep. 9, 2016.
Ganesh "Relaxin-Expressing Fiber Chimeric Oncolytic Adenovirus Prolongs Survival of Tumor-Bearing Mice", Cancer Research, XP009153328, 67(9): 4399-4407, Published Online May 4, 2007.
Jung et al. "Relaxin-Expressing Oncolytic Adenovirus Induces Remodeling of Physical and Immunological Aspects of Cold Tumor to Potentiate PD-1 Blockade", Journal of ImmunoTherapy of Cancer, XP055753373, 8(2): e00763-1-e00763-16, Aug. 2020.
Kaufman et al. "Oncolytic Viruses: A New Class of Immunotherapy Drugs", Nature Reviews Drug Discovery, XP055266462, 14(9): 642-662, Sep. 2015.

(Continued)

*Primary Examiner* — Scott Long
(74) *Attorney, Agent, or Firm* — Sughrue Mion, PLLC

(57) ABSTRACT

The present invention relates to an anticancer composition comprising a tumor-specific oncolytic adenovirus and an immune checkpoint inhibitor. The recombinant adenovirus having IL-12 and shVEGF, or IL-12 and GM-CSF-RLX inserted therein, according to the present invention, exhibits an excellent anticancer effect by enhancing immune functions, and such anticancer effect has been confirmed to be notably enhanced through concomitant administration with an immune checkpoint inhibitor, and thus the present invention may be used as a key technique in the field of cancer treatment.

11 Claims, 22 Drawing Sheets

Specification includes a Sequence Listing.

(56) References Cited

OTHER PUBLICATIONS

Kim et al. "Relaxin Expression From Tumor-Targeting Adenoviruses and Its Intratumoral Spread, Apoptosis Induction, and Efficacy", Journal of the National Cancer Institute, XP002480992, 98(20): 1482-1493, Oct. 18, 2006.

Zhang et al. "Optimizing DC Vaccination by Combination With Oncolytic Adenovirus Coexpressing IL-12 and GM-CSF", Molecular Therapy, XP055070307, 19(8): 1558-1568, Published Online Apr. 5, 2011.

Search Report dated Apr. 14, 2020 from the (ROSPatent), Federal Government Institution of Industrial Property of the Federal Service of Intellectual Property, Patents and Trademark of the Russian Federation Re. Application No. 2019126842. ( 2 Pages).

International Search Report and the Written Opinion dated May 24, 2018 From the International Searching Authority Re. Application No. PCT/KR2018/002439 and Its Translation of Search Report Into English. (17 Pages).

Ahn et al. "Oncolytic Adenovirus Coexpressing Interleukin-12 and ShVEGF Restores Antitumor Immune Function and Enhances Antitumor Efficacy", Oncotarget, 7(51): 84965-84980, Published Online Nov. 4, 2016.

Choi "Enhanced Anti-Tumor Effect of Oncolytic Adenovirus Expressing IL12 and GM-CSF", Doctoral Thesis, Department of Medical Science, The Graduate School, Yonsei University, Seoul, Korea, p. 1-45 & English Abstract, 2009.

Lee "Anti-Tumor Effect Mediated by Replicating Adenoviruses Expressing Relaxin, Decorin, IL-12 of B7.1", Doctoral Thesis, Department of Medical Science. The Graduate School, Yonsei University, Seoul, Korea, p. 1-122 & English Abstract, 2005.

Rojas et al. "Defining Effective Combinations of Immune Checkpoint Blockade and Oncolytic Virotherapy", Clinical Cancer Research, 21(24): 5543-5551, Published Online Jul. 17, 2015.

* cited by examiner a : PBS
b : αPD-1
c : RdB/IL12/GMCSF-RLX
d : RdB/IL12/GMCSF-RLX + αPD-1 a : PBS
b : αPD-1
c : RdB/IL12/GMCSF-RLX
d : RdB/IL12/GMCSF-RLX + αPD-1 a : PBS
b : αPD-1
c : RdB/IL12/GMCSF-RLX
d : RdB/IL12/GMCSF-RLX + αPD-1 a : PBS
b : αPD-1
c : RdB/IL12/GMCSF-RLX
d : RdB/IL12/GMCSF-RLX + αPD-1

↑ : virus injection
↑ : αPD-1 injection

ANTICANCER COMPOSITION COMPRISING TUMOR-SPECIFIC ONCOLYTIC ADENOVIRUS AND IMMUNE CHECKPOINT INHIBITOR

RELATED APPLICATIONS

This application is a Continuation of PCT Patent Application No. PCT/KR2018/002439 having International filing date of Feb. 28, 2018, which claims the benefit of priority of Korean Patent Application No. 10-2017-0026339 filed on Feb. 28, 2017. The contents of the above applications are all incorporated by reference as if fully set forth herein in their entirety.

SEQUENCE LISTING STATEMENT

The ASCII file, entitled 79274SequenceListing.txt, created on Aug. 28, 2019, comprising 19,254 bytes, submitted concurrently with the filing of this application is incorporated herein by reference.

FIELD AND BACKGROUND OF THE INVENTION

The present invention relates to a tumor-specific oncolytic adenovirus which expresses cytokines and degradation factors for the extracellular matrix, an anticancer composition comprising the tumor-specific oncolytic adenovirus and an immune checkpoint inhibitor.

Despite the rapid development of cancer therapeutic agents, cancer is still one of the diseases with a high death rate worldwide. The main cancer treatment methods conventionally used clinically are surgery, radiation treatment, and anticancer agent treatment methods, or methods of maximally removing cancer cells from patients as a treatment in parallel with the same. However, these treatments exhibit treatment effects only when cancer cells are completely removed in a state where a relatively early cancer is not metastasized, and also kill other normal cells which are rapidly dividing, and thus have a disadvantage in that various side effects may be caused. Accordingly, studies have been recently conducted on the treatment of cancer using the tumor-specific immune activity of the body as an immunotherapeutic method.

However, it is difficult to perform the immune treatment because cancer has the ability not only to cleverly evade and destroy various host immune responses, and as a result continuously maintains the survival of tumors by inducing the immunosuppressive tumor microenvironment, but also to escape from the activated anti-tumor immune response even though the immune system is activated. Accordingly, in order to enhance the immune response against cancer cells by improving the immunosuppressive tumor microenvironment, studies using cytokine genes such as IL-12, IL-18, IL-23, interferon-gamma (IFN-γ), a granulocyte-macrophage colony-stimulating factor (GM-CSF), a tumor necrosis factor-alpha (TNF-α), costimulatory factors such as B7 molecules, dendritic cells (DCs) directly serving as antigen presenting cells (APCs), T cells activated by tumor antigens, natural killer cells (NKCs), and the like have been carried out in various directions. It is known that IL-12 is produced by APCs such as monocytes, macrophages, and DCs, and by directly acting on cytotoxic T-lymphocytes (CTLs) and NK cells that can effectively remove cancer cells activates them, stimulates production of IFN-γ, as well as enhances an ability to kill cancer cells by directly acting on them.

In addition, IL-12 plays an important role in promoting differentiation into T helper 1 (TH1) cells by acting on naïve CD4+ lymphocytes, and thus, activating an anticancer immune response by inducing and enhancing the cell-mediated immune response which plays a pivotal role in the anticancer immune response. Further, VEGF is a signal protein produced by cells that promote angiogenesis and vascularization, and affects T cell precursors in the bone marrow to not only suppress the proliferation and maturation of T cells and dendritic cells, but also play an important function in vascularization, thereby exhibiting a side effect called cancer metastasis. Accordingly, VEGF is not only a promoter of tumor growth, but also acts as a suppressor in anticancer immunity, and VEGF downregulation by VEGF shRNA (short hairpin ribonucleic acid) is expected to restore immune responses and to increase anticancer effects. Furthermore, GM-CSF serves to strengthen the immune responses of CD4+ and CD8+ T cells by stimulating DCs to promote the differentiation of DCs into APCs, and is also involved in the expression regulation of molecules constituting major histocompatibility complex (MHC) class II in primary monocytes. In addition, it has been reported that a strong anticancer immune response is induced by inducing many APCs to gather around tumors due to the effect of expression of GM-CSF in the tumors to effectively process tumor antigens.

Based on this, our laboratory also reported an anti-tumor effect of IL-12 using YKL-1 [Ad-E1B55] as an E1B-55 kDa gene-deleted tumor-selective oncolytic adenovirus, and also reported an anti-tumor effect of GM-CSF using an RdB adenovirus with a tumor-selective killing ability more enhanced, due to the deletion of the E1B gene and a modification in an Rb binding site of E1A. However, although the immunosuppressive tumor microenvironment is improved, there are still many limitations in completely treating cancer due to the low immunogenicity of tumors using an immunotherapeutic method.

SUMMARY OF THE INVENTION

As a result of intensive research on developing an immunotherapy for overcoming the immune surveillance evasion of tumors, the present inventors not only confirmed an excellent anticancer effect of IL-12 and a shVEGF (vascular endothelial growth factor (VEGF)-targeting short hairpin ribonucleic acid)) or IL-12 and GM-CSF-relaxin in vivo by preparing a recombinant adenovirus simultaneously expressing them, but also confirmed that an anticancer effect of the recombinant adenovirus was improved through co-administration with an immune checkpoint inhibitor, thereby completing the present invention based on this.

Accordingly, an object of the present invention is to provide a recombinant adenovirus simultaneously expressing IL-12 and shVEGF, or IL-12 and GM-CSF-Relaxin.

Another object of the present invention is to provide a medicinal use of the recombinant adenovirus for the prevention or treatment of cancer.

Still another object of the present invention is to provide a medicinal use of the recombinant adenovirus for the prevention or treatment of cancer as a combined formulation with an immune checkpoint inhibitor.

However, technical problems to be achieved by the present invention are not limited to the aforementioned problems, and other problems that are not mentioned may be clearly understood by those skilled in the art from the following description.

In order to achieve the objects of the present invention as described above, the present invention provides a recombinant adenovirus comprising a gene encoding interleukin 12 (IL-12); a gene encoding a granulocyte-macrophage colony-stimulating factor (GM-CSF); and a gene encoding relaxin, or a recombinant adenovirus comprising a gene encoding Interleukin 12 (IL-12); and a gene encoding a shRNA suppressing the expression of VEGF.

As an embodiment of the present invention, the recombinant adenovirus may have one or more regions selected from the group consisting of the E1 and E3 regions deleted.

As another embodiment of the present invention, the gene encoding IL-12 may comprise an IL-12A (p35) gene sequence, an IRES sequence, and an IL-12B (p40) gene sequence, and may be inserted into the E1 or E3 region of the recombinant adenovirus.

As another embodiment of the present invention, the gene encoding IL-12 may comprise an IL-12A (p35) gene sequence, inker, and an IL-12B (p40) gene sequence, and may be inserted into the E1 or E3 region of the recombinant adenovirus. As still another embodiment of the present invention, the genes encoding GM-CSF and relaxin may comprise a GM-CSF gene sequence, an IRES sequence, and a relaxin gene sequence, and may be inserted into the E1 or E3 region of the recombinant adenovirus.

As yet another embodiment of the present invention, the gene encoding a shRNA suppressing the expression of VEGF may bind complementarily to mRNA of VEGF, and may be inserted into the E1 or E3 region of the recombinant adenovirus.

Further, the present invention provides a pharmaceutical composition for preventing or treating cancer, the composition including: the recombinant adenovirus; and a pharmaceutically acceptable carrier.

As an embodiment of the present invention, the composition may be co-administered with any one immune checkpoint inhibitor selected from the group consisting of a PD-1 (programmed cell death protein 1) antagonist, a PD-L1 (programmed cell death protein ligand 1) antagonist, a PD-L2 antagonist, a CD27 (cluster of differentiation 27) antagonist, a CD28 antagonist, a CD70 antagonist, a CD80 antagonist, a CD86 antagonist, a CD137 antagonist, a CD276 antagonist, a KIRs (killer-cell immunoglobulin-like receptors) antagonist, a LAG3 (lymphocyte-activation gene 3) antagonist, a TNFRSF4 (tumor necrosis factor receptor superfamily, member 4) antagonist, a GITR (glucocorticoid-induced TNFR-related protein) antagonist, a GITRL (GITR ligand) antagonist, a 4-1BBL (4-1BB ligand) antagonist, a CTLA-4 (cytotoxic T lymphocyte associated antigen 4) antagonist, an A2AR (adenosine A2A receptor) antagonist, a VTCN1 (V-set domain-containing T-cell activation inhibitor 1) antagonist, a BTLA (B- and T-lymphocyte attenuator) antagonist, an IDO (Indoleamine 2,3-dioxygenase) antagonist, a TIM-3 (T-cell immunoglobulin and mucin-domain containing-3) antagonist, a VISTA (V-domain Ig suppressor of T cell activation) antagonist, a KLRA antagonist, and a combination thereof.

As another embodiment of the present invention, the composition may enhance anti-tumor immunity.

As still another embodiment of the present invention, the cancer may be selected from the group consisting of gastric cancer, lung cancer, non-small cell lung cancer, breast cancer, ovarian cancer, liver cancer, bronchial cancer, nasopharyngeal cancer, laryngeal cancer, pancreatic cancer, bladder cancer, colon cancer, cervical cancer, bone cancer, non-small cell bone cancer, hematologic malignancy, skin cancer, head or neck cancer, uterine cancer, colorectal cancer, anal near cancer, colon cancer, fallopian tube cancer, endometrial cancer, vaginal cancer, vulva cancer, Hodgkin's disease, esophageal cancer, small intestine cancer, endocrine cancer, thyroid cancer, parathyroid cancer, adrenal cancer, soft tissue sarcoma, urethral cancer, penile cancer, prostate cancer, chronic or acute leukemia, lymphocytic lymphoma, kidney or hydroureter cancer, renal cell carcinoma, renal pelvic carcinoma, salivary gland cancer, sarcoma cancer, pseudomyxoma peritonei, hepatoblastoma, testicular cancer, glioblastoma, cheilocarcinoma, ovarian germ cell tumors, basal cell carcinoma, multiple myeloma, gallbladder cancer, choroidal melanoma, cancer of the ampulla of Vater, peritoneal cancer, tongue cancer, small cell cancer, pediatric lymphoma, neuroblastoma, duodenal cancer, ureteral cancer, astrocytoma, meningioma, renal pelvis cancer, pudendum cancer, thymus cancer, central nervous system tumors, primary central nervous system lymphoma, spinal cord tumors, brain stem neuroglioma, and pituitary adenoma, and the cancer may also be a recurrent cancer.

The recombinant adenovirus having IL-12 and shVEGF, or IL-12 and GM-CSF-Relaxin inserted therein, according to the present invention, exhibits an excellent anticancer effect by improving immune functions, and such an anticancer effect has been confirmed to be remarkably enhanced through co-administration with an immune checkpoint inhibitor, and thus the present invention may be used as a key technique in the field of cancer treatment.

BRIEF DESCRIPTION OF THE SEVERAL VIEWS OF THE DRAWINGS

The above and other objects, features and advantages of the present disclosure will become more apparent to those of ordinary skill in the art by describing in detail exemplary embodiments thereof with reference to the accompanying drawings, in which:

FIG. 3A is a result confirming a change in volume of tumors, and FIG. 3B is a result confirming a change in survival rate of mice with melanoma. Ad $5\times10^9$ viral particle (VP) (FIG. 3A; an initial tumor volume: 80 to 100 $mm^3$) adenovirus was administered to tumors of C57BL/6 mice on day 1, 3, and 5, and 200 µg of an anti PD-L1 antibody was intraperitoneally administered. The volume of tumors was monitored and recorded daily until the end of the experiment. The red arrow indicates the time when the adenovirus is injected, and the black arrow indicates the time when the antibody is injected.

FIG. 4A is a result confirming a change in volume of tumors, and FIG. 4B is a result confirming a change in survival rate of mice with melanoma.

FIG. 8A is a result confirming a change in volume of tumors, and FIG. 8B is a result confirming a change in survival rate of mice with melanoma.

FIG. 9A is a result confirming a change in volume of tumors, and FIG. 9B is a result confirming a change in survival rate of mice with melanoma.

FIG. 10A is a result confirming a change in volume of secondary tumors when RdB/IL12/shVEGF Ad is administered, and FIG. 10B is a result confirming a change in volume of secondary tumors when RdB/IL12/shVEGF Ad and an immune checkpoint inhibitor (anti PD-1 antibody) are co-administered.

DESCRIPTION OS SPECIFIC EMBODIMENTS OF THE INVENTION

Figure 1:
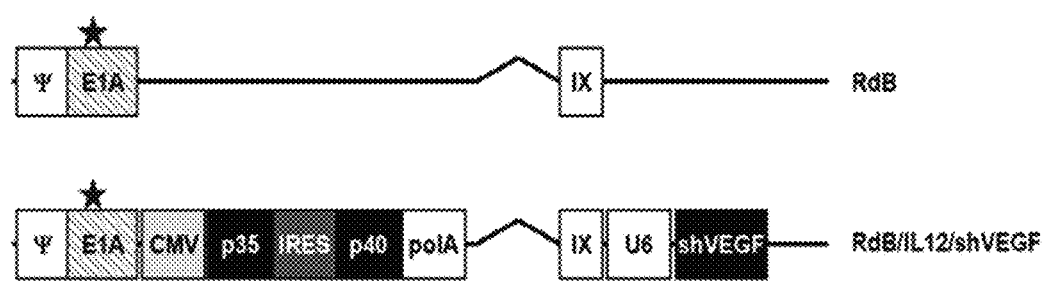
FIG. 1 illustrates characteristics of an oncolytic adenovirus simultaneously expressing IL-12 and shRNA for VEGF, and is a view schematically illustrating the genetic structure of RdB/IL12/shVEGF Ad. An RdB comprises a modified E1A (mutation of open star-Rb proteins binding site), and E1B-19 and E1B-55 kDa (E1B), and E3 region (E3) are deleted; and a mouse IL-12 and a mouse shVEGF are inserted into the E1 or E3 region of the adenoviral genome, respectively.

Hereinafter, the present invention will be described in detail.

The present invention provides a recombinant adenovirus including: a gene encoding Interleukin 12 (IL-12); a gene encoding a granulocyte-macrophage colony-stimulating factor (GM-CSF); and a gene encoding relaxin, or a recombinant adenovirus including: a gene encoding IL-12; and a gene encoding a shRNA suppressing the expression of VEGF.

Although an immune gene therapy for cancer has developed as a more promising approach, tumors have also created numerous strategies to avoid the immune surveillance system. In order to overcome these obstacles and enhance the effects of anticancer immunity, an oncolytic adenovirus (RdB/IL12/shVEGF Ad, RdB/IL12/GMCSF-RLX Ad) system simultaneously expressing IL-12 and a vascular endothelial growth factor (VEGF) short hairpin RNA (shRNA) or IL-12 and GM-CSF-Relaxin was constructed as an appropriate therapeutic adjuvant for restoring immunosuppression and increasing anticancer immunity. IL-12 serves to increase anti-tumor immunity by inducing the differentiation of T helper 1 cells and activating the cytotoxicity of cytotoxic T lymphocytes and natural killer cells. It is known that shVEGF and GM-CSF serve to strengthen the immune response of CD4+ and CD8+ T cells by promoting the proliferation and maturation of T cells and dendritic cells and stimulating DCs to promote the differentiation of DCs into APCs, respectively, and these effects are expected to further amplify the IL-12 function. Thus, the present inventors attempted immune gene therapy using a technical feature of an adenovirus simultaneously expressing IL-2 and shVEGF, or IL-12 and GM-CSF-Relaxin in tumors for the first time. In an example of the present invention, as a result of administering the recombinant adenovirus (RdB/IL12/shVEGF Ad, RdB/IL12/GMCSF-RLX Ad) to a melanoma animal model, it was experimentally confirmed that the tumor growth inhibition rate, complete remission rate, and survival rate of mice were increased.

In addition, IL-12 has drawn much attention as a core cytokine for anticancer immunotherapy, and in particular, in an anticancer immunotherapeutic method for patients with impaired immunity in the body, repeated administration of IL-12 has been frequently considered in order to obtain effective therapeutic efficacy. However, the IL-12 is clinically known to have the cytokine-associated toxicity in the whole body, particularly, the kidneys, and thus has a technical limitation that the IL-12 has to be used as a cancer therapeutic agent within a limited dose range. Based on this technical background, the recombinant adenovirus simultaneously expressing the IL-12 gene according to the present invention and an additional gene has another technical feature of solving the toxicity problem for normal cells due to the high dose and repeated administration of IL-12, which has been pointed out as a limitation of the anticancer immunotherapy in the related art, by inducing a high oncolytic effect even at a low viral titer.

Accordingly, the recombinant adenovirus of the present invention is characterized by including a gene encoding IL-12 and including any one of a gene encoding GM-CSF, a gene encoding relaxin, and a gene encoding a shRNA suppressing the expression of VEGF.

Interleukin-12 (IL-12) is a disulfide-linked heterodimer which is composed of a 40 kDa subunit (p40 subunit, p40) encoded by IL-12B (or Interleukin-12 subunit beta) and a 35 kDa subunit (p35 subunit or p35) encoded by IL-12A (or Interleukin-12 subunit alpha) and has a molecular weight of 75 kDa. IL-12 binds to receptors on the cell surface of activated T cells, B cells, and NK cells produced by antigen presenting cells such as macrophages (Desai, B. B., et al., J. Immunol., 148:3125-3132 (1992); Vogel, L. A., et al., Int. Immunol., 8:1955-1962, (1996)). IL-12 has been reported to be an important co-stimulator of Th1 clone proliferation (Kennedy et al., Eur. J. Immunol. 24:2271-2278, 1994), and is known to increase the production of IgG2a antibodies in serum (Morris, S. C., et al., J. Immunol. 152:1047-1056 (1994); Germann, T. M., et al., Eur. J. Immunol., 25:823-829 (1995); Sher, A., et al., Ann. N.Y. Acad. Sci., 795:202-207 (1996); Buchanan, J. M., et al., Int. Immunol., 7:1519-1528 (1995); Metzger, D. W. et al., Eur. J. Imunol., 27:1958-1965 (1997)). Further, it has been reported that administration of IL-12 can temporarily reduce the production of IgG1 antibody, suggesting that IL-12 inhibits the Th2 immune response (Morris, S. C., et al., J. Immunol. 152:1047-1056 (1994); McKnight, A. J., J. Immunol. 152:2172-2179 (1994); Buchanan, J. M., et al., Int. Immunol., 7:1519-1528 (1995)).

Cloning and purification of IL-12 is disclosed in WO 92/05256, WO 90/05147, and EP 322,827, the contents of which are incorporated herein by reference. The recombinant adenoviruses of the present invention comprise an IL-12 coding nucleotide sequence in an expressible form and can secrete IL-12 in tumor cells to enhance antitumor immune responses.

In order to efficiently express IL-12 using the recombinant adenovirus of the present invention, an expression system can be constructed using both the p35 subunit coding nucleotide sequence and the p40 subunit coding nucleotide sequence. In the present invention, the p35 subunit and the p40 subunit comprise not only the subunits illustrated in the embodiments of the present invention but also all the analogues of the subunits that can perform the unique function of each subunit.

In one embodiment of the present invention, the amino acid sequences of the human p35 and p40 subunits that may be used in the present invention are those sequences of GenBank accession numbers AAD56385 and AAD56386, respectively (if the amino acid sequences of the mouse p35 and p40 subunits are to be expressed, AAA39292 and AAA39296).

In one embodiment of the present invention, the nucleotide sequences encoding the p35 and p40 subunits that may be used in the present invention are IL-12A (p35) gene sequence and an IL-12B (p40) gene sequence encoding the amino acid sequences of the p35 and p40 subunits. The nucleotide sequences encoding the human p35 and p40 subunits can be found in GenBank accession numbers AF180562 and AF180563, and preferably the nucleotide sequences corresponding to the coding sequence (CDS) can be used (If using the mouse p35 and p40 nucleotide sequences, refer to the CDS sequence in each of the sequences listed in GenBank Accession Numbers M86672 and M86671).

Also, the "gene encoding IL-12" used in the present invention comprises an IL-12A (p35) gene sequence and an IL-12B (p40) gene sequence, and may comprise an IRES sequence or linker sequence between the IL-12A (p35) gene sequence and the IL-12B (p40) gene sequence for the effective translation of a viral protein. Preferably, in one embodiment of the present invention, the IL-12A (p35) gene sequence may comprise or consist of a sequence of SEQ ID No. 1 (mouse), SEQ ID No. 10 (human), or SEQ ID No. 11 (human); the IL-12B (p40) gene sequence may comprise or consist of a sequence of SEQ ID No. 2 (mouse), SEQ ID No. 12 (human), or SEQ ID No. 13 (human); the IRES sequence may comprise or consist of a sequence of SEQ ID No. 3 or SEQ ID No. 15; and the linker sequence may comprise or consist of a sequence of SEQ ID No. 14.

The gene encoding IL-12 of the present invention may comprise or consist a sequence of SEQ ID No. 16 (human IL-12A-linker-IL-12B) or SEQ ID No. 17 (human IL-12A-IRES-IL-12B), but are not limited thereto. The IL-12 serves to increase anti-tumor immunity by inducing the differentiation of T helper 1 cells and activating the cytotoxicity of cytotoxic T lymphocytes and natural killer cells.

The "gene encoding GM-CSF" and the "gene encoding relaxin" used in the present invention comprise a GM-CSF gene sequence and a relaxin gene sequence, respectively, and may also comprise an IRES sequence between the GM-CSF gene sequence and the relaxin gene sequence. Preferably, the GM-CSF gene sequence may comprise or consist of the sequence of SEQ ID No. 4 (mouse) or SEQ ID No. 18 (human); the relaxin gene sequence may comprise or consist of the sequence of SEQ ID No. 5 (human); the IRES sequence may comprise or consist a sequence of SEQ ID No. 3 or SEQ ID No. 15 but are not limited thereto.

The "gene encoding a shRNA suppressing the expression of VEGF" used in the present invention has a hairpin structure, and refers to a gene capable of mediating RNA interference or gene silencing. The gene comprises a sequence complementary to VEGF mRNA, and the term "complementary" means including not only the 100% complementary case, but also the incomplete complementarity sufficient to be able to suppress the expression of the VEGF gene through the RNA interference mechanism, and means preferably 90% complementarity, more preferably 98% complementarity, and most preferably 100% complementarity. In the present specification, the case of expressing the 100% complementarity is specifically described as completely complementary. In the present invention, although the gene is also described as shVEGF, but is not limited thereto, the gene may bind complementarily to the mRNA of VEGF, which is represented by SEQ ID No. 6 (mouse) or 7 (human), to suppress the expression of VEGF. In one embodiment of the present invention, a shRNA sequence suppressing the expression of mouse VEGF may comprise or consist of SEQ ID No. 8 and SEQ ID No. 9.

It is interpreted that the gene sequences also comprise a gene sequence exhibiting substantial identity or substantial similarity. The aforementioned substantial identity refers to a random sequence differing from the sequence of the present invention and having at least 80% homology, more preferably 90% homology, and most preferably 95% homology to the sequence of the present invention, when it is aligned to correspond to the sequence of the present invention as much as possible, and the aligned sequences are analyzed using an algorithm typically used in the art. The aforementioned substantial similarity collectively refers to all of the changes in a gene sequence, such as deletion or insertion of one or more bases, which do not affect the object of the present invention of minimizing homologous recombination with a recombinant adenovirus vector. Therefore, the gene sequence of the present invention is not limited to the sequences of exemplified SEQ ID NOS. 1 to 18, and is interpreted to be included in the scope of the rights of the present invention as long as the sequence does not substantially affect the activity of the final product desired in the present invention.

Meanwhile, as the recombinant adenovirus of the present invention, an oncolytic adenovirus widely known in the art may be used. In an example of the present invention, the recombinant adenovirus comprises an activated E1A gene and an inactivated E1B-19 gene, an inactivated E1B-55 gene, or an inactivated E1B-19/E1B-55 gene. In the present specification, the term inactivation used in conjunction with a gene means that the transcription and/or translation of the gene is not normally performed, and the function of a normal protein encoded by the gene is not exhibited. For example, the inactivated E1B-19 gene is a gene incapable of producing the activated E1B-19 kDa protein by a modification (substitution, addition, and partial or whole deletion) in the gene. The deletion of E1B-19 may increase the ability to kill cells, and the deletion of the E1B-55 gene makes a recombinant adenovirus tumor-specific (see Korean Patent Application No. 2002-23760). The term "deletion" used in conjunction with a viral genomic sequence in the present specification has a meaning including complete deletion and partial deletion of the corresponding sequence.

According to an embodiment of the present invention, the recombinant adenovirus comprises an E1A region, has an E1B region, that is, E1B-19 kDa and 55 kDa (E1B) deleted, and an E3 region (E3) deleted. The recombinant adenovirus including the E1A gene will have replicable characteristics. The gene encoding IL-12 is inserted into the deleted E1B region of the recombinant adenovirus, and the genes encoding GM-CSF and relaxin or the gene encoding a shRNA suppressing the expression of VEGF is inserted into the E3 region. Meanwhile, the E1A site has a modification in which the Glu 45 residue is substituted with Gly and a modification and in which the sequence of amino acids 121 to 127 is wholly substituted with Gly, in a nucleotide sequence encoding Rb binding site located in the E1A gene sequence.

Meanwhile, viruses other than the adenovirus may also be used in the present invention. The virus which may be used in the present invention may preferably be vaccinia viruses (Puhlmann M. et al., Human Gene Therapy 10:649-657 (1999)), lentiviruses (Wang G. et al., J. Clin. Invest. 104(11): R55-62 (1999)), or herpes simplex viruses (Chamber R., et al., Proc. Natl. Acad. Sci USA 92:1411-1415 (1995)) but is not limited thereto.

The recombinant adenovirus used in the present invention comprises a promoter that is operable in animal cells, preferably mammal cells. A promoter suitable for the present invention comprises a promoter derived from a mammalian virus and a promoter derived from the genome of mammalian cells, and comprises, for example, a cytomegalovirus (CMV) promoter, a U6 promoter and an H1 promoter, a murine leukemia virus (MLU) long terminal repeat (LTR) promoter, an adenovirus early promoter, an adenovirus late promoter, a vaccina virus 7.5K promoter, an simian virus 40 (SV40) promoter, a Herpes simplex virus-thymidine kinase (HSV tk) promoter, an rous sarcoma virus (RSV) promoter, an elongation factor-1 alpha (EF1 α) promoter, a methallothionin promoter, a β-actin promoter, a human IL-2 gene promoter, a human IFN gene promoter, a human IL-4 gene promoter, a human lymphotoxin gene promoter, a human GM-CSF gene promoter, an inducible promoter, a cancer cell-specific promoter [for example, a telomerase reverse transcriptase (TERT) promoter, a modified TERT promoter, a prostate-specific antigen (PSA) promoter, a prostate-specific membrane antigen (PSMA) promoter, a carcinoembryonic antigen (CEA) promoter, a Survivin promoter, an E2F promoter, a modified E2F promoter, an alpha-fetoprotein (AFP) promoter, a modified AFP promoter, an E2F-AFP hybrid promoter, and an E2F-TERT hybrid promoter], a tissue-specific promoter (for example, an albumin promoter), a human phosphoglycerate kinase (PGK) promoter, and a mouse phosphoglycerate kinase (PGK) promoter, but is not limited thereto. Most preferably, the promoter is a CMV promoter.

It is preferred that in an expression construct for expressing a trans gene, a polyadenylation sequence binds downstream of the trans gene. The polyadenylation sequence comprises a bovine growth hormone terminator (Gimmi, E. R., et al., Nucleic Acids Res. 17:6983-6998 (1989)), an SV40-derived polyadenylation sequence (Schek, N, et al., Mol. Cell Biol. 12:5386-5393 (1992)), HIV-1 polyA (Klasens, B. I. F., et al., Nucleic Acids Res. 26:1870-1876 (1998)), β-globin polyA (Gil, A., et al, Cell 49:399-406

(1987)), HSV TK polyA (Cole, C. N. and T. P. Stacy, Mol. Cell. Biol. 5:2104-2113 (1985)), or polyomavirus polyA (Batt, D. B and G. G. Biol. 15:4783-4790 (1995)), but is not limited thereto.

In the recombinant adenovirus used in the present invention, the IL-12 gene sequence, the GM-CSF-Relaxin gene sequence, or the shVEGF gene sequence are operably linked to a promoter. As used herein, the term "operably linked" refers to a functional binding between a nucleic acid expression regulatory sequence (for example: an array of a promoter, a signal sequence, and a transcription regulating factor-binding site) and a different nucleic acid sequence, and accordingly, the regulatory sequence regulates the transcription and/or translation of the different nucleic acid sequence.

The recombinant adenovirus of the present invention may further comprise an antibiotic resistance gene and a reporter gene (for example, green fluorescence protein (GFP), luciferase and β-glucuronidase) as selective markers. The antibiotic resistance gene comprises an antibiotic resistance gene typically used in the art, for example, a gene imparting resistance to ampicillin, gentamycin, carbenicillin, chloramphenicol, streptomycin, kanamycin, geneticin, neomycin and tetracycline, and preferably, is a neomycin resistance gene. The aforementioned selective marker may be expressed even in an expression system connected by a separate promoter or an IRES (internal ribosome entry site), 2A systems (F2A system, P2A system, T2A system), and the IRES that may be used in the present invention is a regulatory sequence that is found in RNAs of some types of viruses and cells.

Another aspect of the present invention provides: a pharmaceutical composition for preventing or treating cancer, the composition including the recombinant adenovirus; and a pharmaceutically acceptable carrier; a medicinal use of the recombinant adenovirus for the prevention or treatment of cancer; and a method for treating cancer, the method including a step of administering a therapeutically effective amount of the recombinant adenovirus to an individual.

Since the pharmaceutical composition of the present invention uses the above-described recombinant adenovirus, the description of the content common between the two will be omitted in order to avoid the excessive complexity of the present specification.

As used herein the term "prevention" refers to all actions that suppress cancer (tumors) or delay the onset of the cancer (tumors) by administering the pharmaceutical composition according to the present invention.

As used herein, the term "treatment" refers to all actions that ameliorate or beneficially change symptoms for cancer (tumors) by administering the pharmaceutical composition according to the present invention.

In the present invention, "an individual" refers to a subject in need of treatment of a disease, and more specifically, refers to a mammal such as a human or a non-human primate, a rodent (a rat, a mouse, a guinea pig, and the like), a mouse, a dog, a cat, a horse, a cow, a sheep, a pig, a goat, a camel, and an antelope.

"Cancer", which is a disease to be prevented or treated by the pharmaceutical composition of the present invention, collectively refers to diseases caused by cells having aggressive characteristics in which the cells ignore normal growth limits and divide and grow, invasive characteristics to infiltrate surrounding tissues, and metastatic characteristics of spreading to other sites in the body. In the present invention, the cancer is used in the same sense as a malignant tumor, and may comprise a solid tumor and a blood borne tumor.

For example, the cancer may be any one selected from the group consisting of gastric cancer, lung cancer, non-small cell lung cancer, breast cancer, ovarian cancer, liver cancer, bronchial cancer, nasopharyngeal cancer, laryngeal cancer, pancreatic cancer, bladder cancer, colon cancer, cervical cancer, bone cancer, non-small cell bone cancer, hematologic malignancy, skin cancer, head or neck cancer, uterine cancer, colorectal cancer, anal near cancer, colon cancer, fallopian tube cancer, endometrial cancer, vaginal cancer, vulva cancer, Hodgkin's disease, esophageal cancer, small intestine cancer, endocrine cancer, thyroid cancer, parathyroid cancer, adrenal cancer, soft tissue sarcoma, urethral cancer, penile cancer, prostate cancer, chronic or acute leukemia, lymphocytic lymphoma, kidney or hydroureter cancer, renal cell carcinoma, renal pelvic carcinoma, salivary gland cancer, sarcoma cancer, pseudomyxoma peritonei, hepatoblastoma, testicular cancer, glioblastoma, cheilocarcinoma, ovarian germ cell tumors, basal cell carcinoma, multiple myeloma, gallbladder cancer, choroidal melanoma, cancer of the ampulla of Vater, peritoneal cancer, tongue cancer, small cell cancer, pediatric lymphoma, neuroblastoma, duodenal cancer, ureteral cancer, astrocytoma, meningioma, renal pelvis cancer, pudendum cancer, thymus cancer, central nervous system (CNS) tumors, primary central nervous system lymphoma, spinal cord tumors, brain stem neuroglioma, and pituitary adenoma, and may also be a recurrent cancer, but is not limited thereto.

Meanwhile, the pharmaceutical composition of the present invention may additionally comprise an immune checkpoint inhibitor.

As used herein, the term "immune checkpoint" collectively refers to a protein involved in causing stimulating or suppressing signals of an immune response on the surface of immune cells, and cancer cells evade the surveillance network of the immune system by being manipulated such that the stimulation of the immune response and the resulting inhibition of cancer cells are not properly performed through the immune checkpoint. Preferably, the immune checkpoint protein may be a PD-1 antagonist, a PD-L1 antagonist, a PD-L2 antagonist, a CD27 antagonist, a CD28 antagonist, a CD70 antagonist, a CD80 antagonist, a CD86 antagonist, a CD137 antagonist, a CD276 antagonist, a KIRs antagonist, a LAG3 antagonist, a TNFRSF4 antagonist, a GITR antagonist, a GITRL antagonist, a 4-1BBL antagonist, a CTLA-4 antagonist, an A2AR antagonist, a VTCN1 antagonist, a BTLA antagonist, an IDO antagonist, a TIM-3 antagonist, a VISTA antagonist, a KLRA antagonist, and a combination thereof, but is not limited thereto.

The immune checkpoint inhibitor is an antagonist or antibody targeting the immune checkpoint protein, and exhibits an anticancer effect caused by an immune response by enhancing a protein which stimulates the immune response or blocking a protein which suppresses the immune response. Since the immune checkpoint inhibitor uses an immune response system which is excellent in memory ability in addition to advantages of fewer side effects such as emesis or alopecia than general cytotoxic anticancer agents and large therapeutic effects, the therapeutic effect may be sustained for a long period of time even after the administration of a drug is stopped, but the enhancement of the anticancer effect through a co-administration with the recombinant adenovirus has not been known. Thus, the present inventors attempted co-administration with an immune checkpoint inhibitor in order to enhance the anti-cancer effect of the recombinant adenovirus, and there is another technical feature in that there is provided a medicinal use of the recombinant adenovirus for the prevention or treatment of cancer as a co-administration formulation with the immune checkpoint inhibitor.

The pharmaceutical composition of the present invention may comprise a pharmaceutically acceptable carrier in addition to the active ingredient. In this case, the pharmaceutically acceptable carrier is typically used during the formulation, and comprises lactose, dextrose, sucrose, sorbitol, mannitol, starch, gum acacia, calcium phosphate, alginate, gelatin, calcium silicate, microcrystalline cellulose, polyvinylpyrrolidinone, cellulose, water, syrup, methylcellulose, methyl hydroxybenzoate, propyl hydroxybenzoate, talc, magnesium stearate, mineral oil, and the like, but is not limited thereto. Furthermore, the pharmaceutically acceptable carrier may further comprise a lubricant, a wetting agent, a sweetening agent, a flavoring agent, an emulsifier, a suspending agent, a preservative, and the like, in addition to the aforementioned ingredients. Suitable pharmaceutically acceptable carriers and formulations are described in detail in Remington's Pharmaceutical Sciences (19th ed., 1995).

The pharmaceutical composition of the present invention may be administered orally or parenterally (for example, intravenously, subcutaneously, intraperitoneally, or applied topically), and according to an example of the present invention, the anti-tumor immunity enhancing composition of the present invention may be preferably directly administered intratumorally. The dose varies depending on the patient's condition and body weight, severity of the disease, drug form, administration route, and duration, but may be suitably selected by those skilled in the art.

The pharmaceutical composition of the present invention is administered in a pharmaceutically effective amount. In the present invention, "pharmaceutically effective amount" means an amount sufficient to treat diseases at a reasonable benefit/risk ratio applicable to medical treatment, and an effective dosage level may be determined according to factors including type of disease of patients, the severity of disease, the activity of drugs, sensitivity to drugs, administration time, administration route, excretion rate, treatment period, and simultaneously used drugs, and other factors well known in the medical field. Another pharmaceutical composition according to the present invention may be administered as an individual therapeutic agent or in combination with other therapeutic agents, may be administered sequentially or simultaneously with therapeutic agents in the related art, and may be administered in a single dose or multiple doses. It is important to administer the composition in a minimum amount that can obtain the maximum effect without any side effects, in consideration of all the aforementioned factors, and this amount may be easily determined by those skilled in the art.

Hereinafter, preferred Examples for helping the understanding of the present invention will be suggested. However, the following Examples are provided only to more easily understand the present invention, and the contents of the present invention are not limited by the following Examples.

EXAMPLES

Experimental Materials and Experimental Methods

1. Animal Experiment 6-week to 8-week old male C57BL/6 mice were purchased from Charles River Laboratories International, Inc. (Wilmington, Mass.) and bred in a laminar air flow cabinet under a pathogen free condition. All animal experiments were carried out under the approval of the Association for Assessment and Accreditation of Laboratory Animal Care (AAALAC), and performed in accordance with the guidelines established by the University of Hanyang Institutional Animal Care and Use Committee.

2. Manufacture of Oncolytic Adenovirus

Figure 2:
FIG. 2 illustrates characteristics of an oncolytic adenovirus simultaneously expressing IL-12 and GM-CSF and relaxin (GMCSF-Relaxin), and is a view schematically illustrating the genetic structure of RdB/IL12/GMCSF-RLX Ad. IL-12 and GMCSF-Relaxin are inserted into the E1 or E3 region of the adenoviral genome, respectively. GMCSF and relaxin may also be expressed by an expression system linked by an IRES (internal ribosome entry site), and in the present invention, the IRES is a regulatory sequence found in the RNAs of several viruses and cells.

An adenovirus (Ad), in which IL-12 and GM-CSF-Relaxin or shVEGF were introduced into the E1 region and the E3 region, respectively, was manufactured as illustrated in FIGS. 1 and 2.

Specifically, in order to construct an Ad E1 shuttle vector expressing IL-12, a pXC1RdB/IL12 E1 shuttle vector was manufactured by excising a mouse IL-12 gene from pCA14/IL12 and sub-cloning the gene into a pXC1RdB E1 shuttle vector. Further, in order to construct a shVEGF-expressing E3 shuttle vector, full-length mouse shVEGF complementary DNA was cloned by RT-PCR using total RNA obtained from bone marrow-derived active dendritic cells. The shVEGF complementary DNA (nucleotides 53-982 of the National Center for Biotechnology Information L15435) was manufactured using the following primer set: sense (5'-gatcccggaaggagagcagaagtcccatgttcaagaga-catgggacttctgctctccttttttttggaaa-3'), antisense (5'-tttc-caaaaaaa aaggagagcagaagtcccatgtctcttgaa-catgggacttctgctctccttccgggatc-3'). The PCR product was digested with BamHI/Hind III, and then cloned in a BamHI/Hind III-treated pSP72 E3/CMV-polA Ad E3 shuttle vector, thereby manufacturing a pSP72 E3/shVEGF E3 shuttle vector. Further, a pSP72 E3/GMCSF-RLX E3 shuttle vector was manufactured by cloning GMCSF-IRES-Relaxin gene in a pSP72 E3/CMV-polA Ad E3 shuttle vector.

For homologous recombination, E. coli BJ5183 was transformed simultaneously with the pXC1RdB/IL12 E1 shuttle vector and pdE1/shVEGF or pdE1/GMCSF-RLX, thereby manufacturing pRdB/IL12/shVEGF Ad and pRdB/IL12/GMCSF-RLX Ad. All viruses were manufactured using 293 cells, and the purification, titration, and quality analysis of the adenovirus were carried out according to the prior art.

3. Evaluation of Anticancer Effect Using Animal Model

B16-F10 cells ($5 \times 10^5$) were injected subcutaneously into the right flank of 6- to 7-week old male C57BL/6 immune-competent mice. When the tumor volume reached approximately 100 mm3, the mice were divided into groups with similar tumor sizes, and the oncolytic adenoviruses (RdB/IL12/shVEGF Ad; RdB/IL12/GMCSF-RLX Ad) were administered intratumorally at a concentration of $5 \times 10^9$ VP on day 1, 3, and 5. In addition, in order to confirm the anticancer effect according to the co-administration with an immune checkpoint inhibitor, an anti PD-L1 antibody, an anti PD-1 antibody, and an anti CTLA-4 antibody as immune checkpoint inhibitors were administered intraperitoneally at a concentration of 200 μg to the oncolytic adenovirus-administered mice on day 3, 6, and 9, and in order to further evaluate a synergistic effect by the co-administration with the immune checkpoint inhibitor, the same experiment as described above was performed again using the oncolytic adenovirus at a dose ($1 \times 10^9$ VP) which is five times lower than that of the previous experiment using $5 \times 10^9$ VP. Meanwhile, in the present experiment, a PBS-treated group (PBS) and groups treated with the immune checkpoint inhibitor alone (anti PD-L1 antibody, anti PD-1 antibody, and anti CTLA-4 antibody) were used as controls.

Thereafter, an anticancer effect was evaluated using an animal model by measuring a perpendicular tumor diameter using calipers to monitor the growth of tumors every day and confirming a change in survival rate over time. Meanwhile, tumor volume was calculated using the following formula: volume=0.523 L (W)2, in which L indicates a length and W indicates a width.

4. Evaluation of Anticancer Effect by Immune Memory

On day 50 after a primary tumor was injected into animal models in which melanoma was induced, a secondary tumor was reinjected (rechallenge) into successfully treated mice (on day 25 from the time point when the primary tumor could not be promoted). Thereafter, in the same manner as described above, an anti-tumor immune memory effect was evaluated by measuring a perpendicular tumor diameter to monitor the growth of tumors every other day and calculating an average tumor volume. In the present experiment, a group in which melanoma was induced in normal mice (Normal) was used as a control.

5. Statistical Analysis

All data was expressed as mean±standard error. Comparisons were made using Stat View software (Abacus Concepts, Inc., Berkeley, Calif.) and the Mann-Whitney test (non-parametric rank sum test). P values equal to or less than 0.05 indicate statistically significance (*, $P<0.05$; **, $P<0.01$).

Experimental Results

1. Confirmation of Anticancer Effect in Melanoma Mice

The present inventors intended to confirm the anticancer effect of the recombinant adenovirus and/or the immune checkpoint inhibitor by comparing the volume of a tumor injected into melanoma mice, the presence of complete remission, and the survival rate of the mice.

Figure 3A:
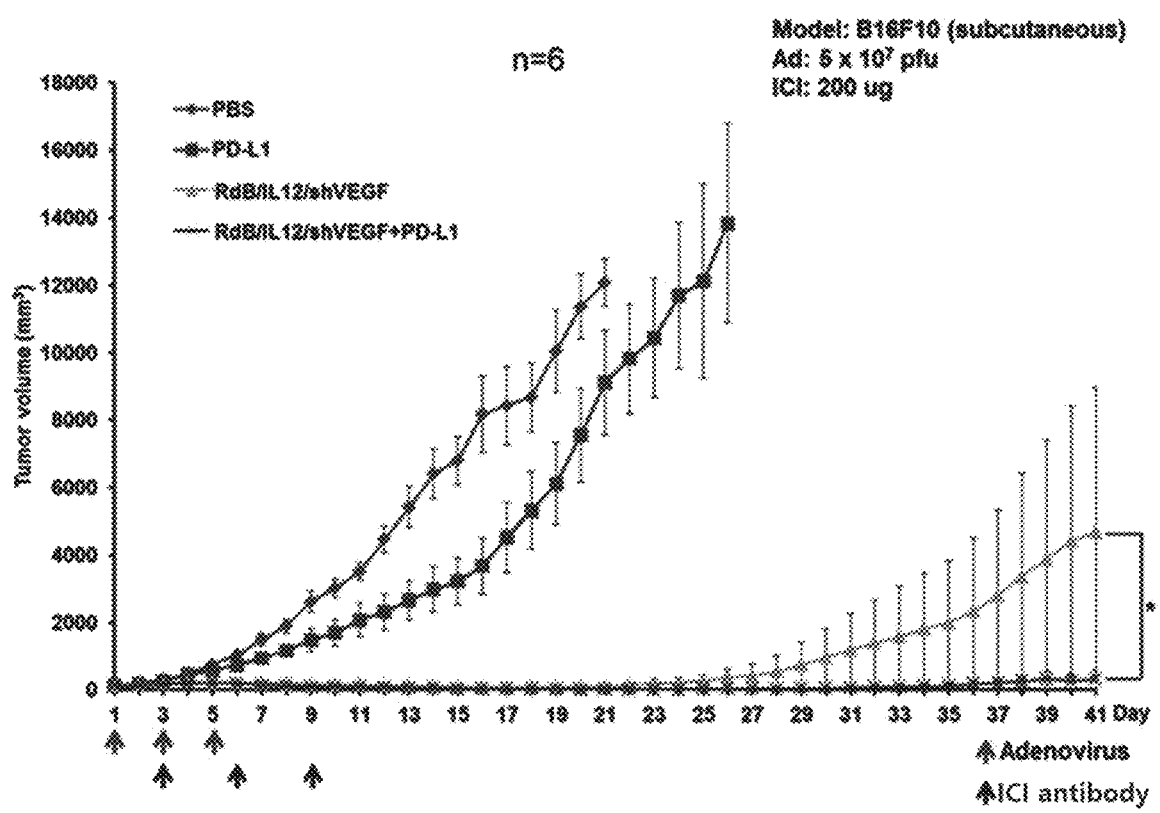
FIGS. 3A and 3B confirm an anticancer effect according to the administration of RdB/IL12/shVEGF Ad and the co-administration of RdB/IL12/shVEGF Ad and an immune checkpoint inhibitor (anti PD-L1 antibody; αPD-L1) in mice with melanoma.
Figure 3B:
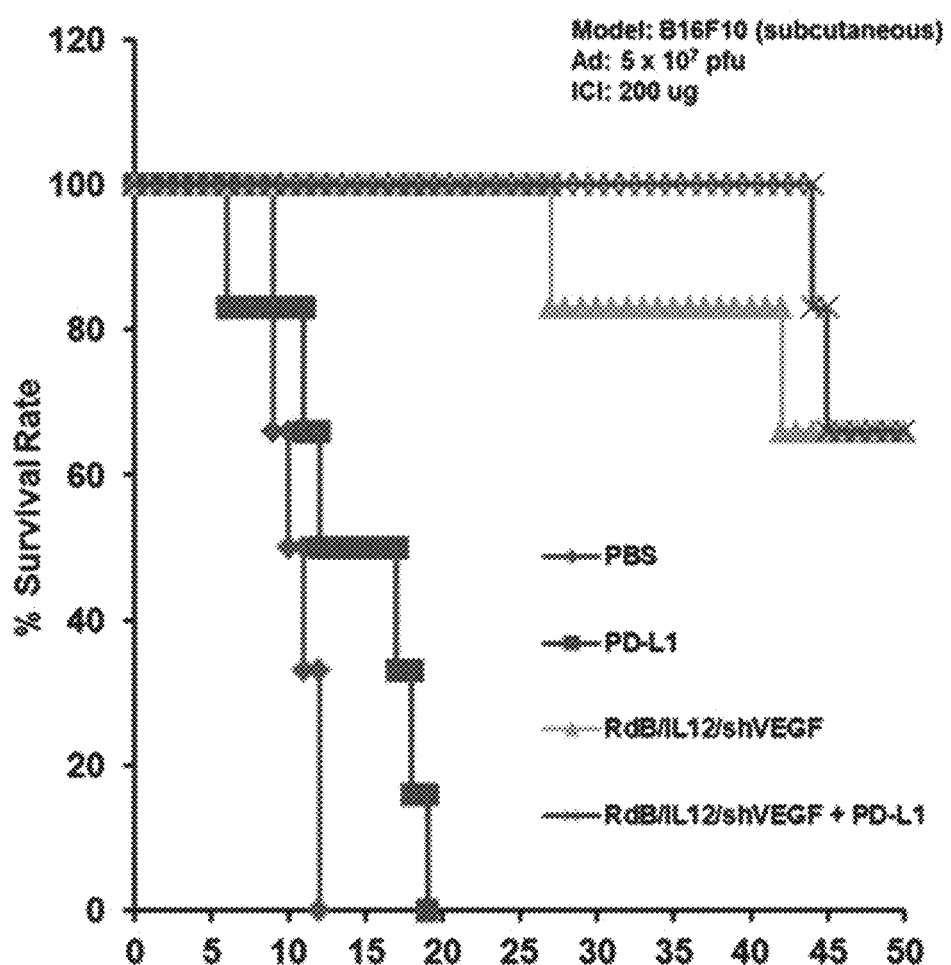
Figure 4A:
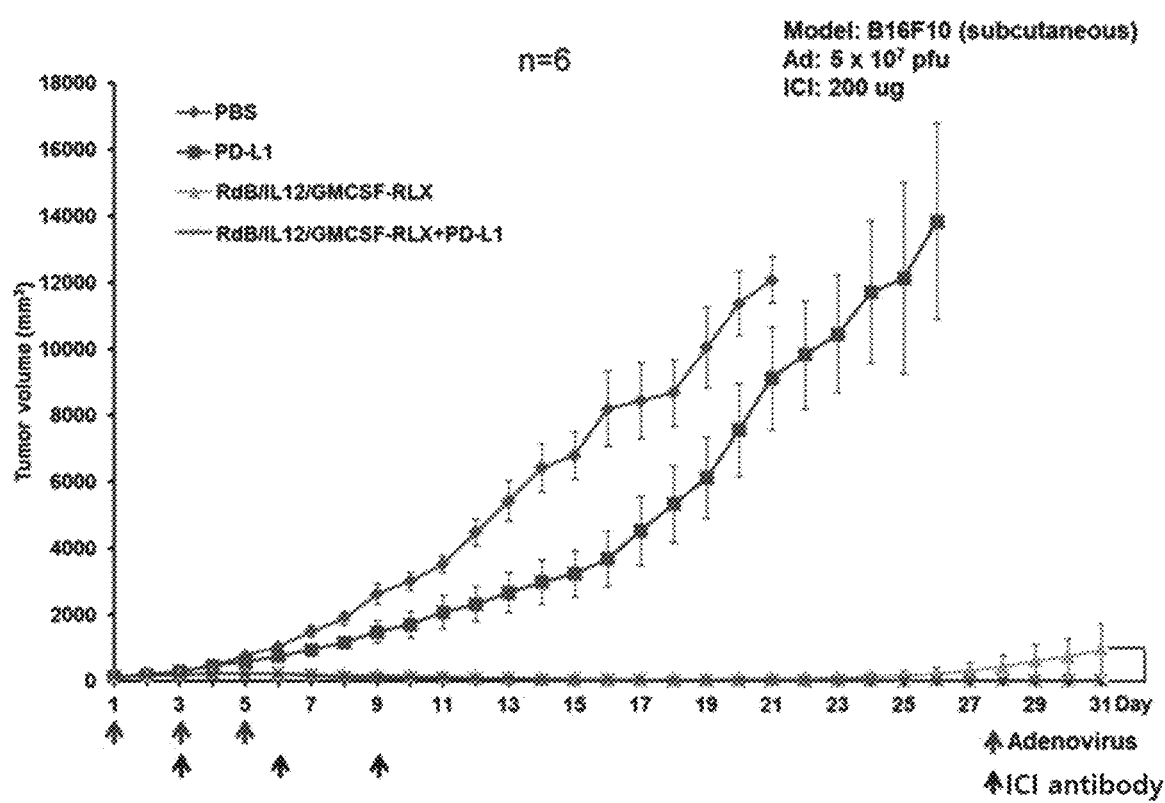
FIGS. 4A and 4B confirm an anticancer effect according to the administration of RdB/IL12/GMCSF-RLX Ad and the co-administration of RdB/IL12/GMCSF-RLX Ad and an immune checkpoint inhibitor (anti PD-L1 antibody) in mice with melanoma.
Figure 4B:
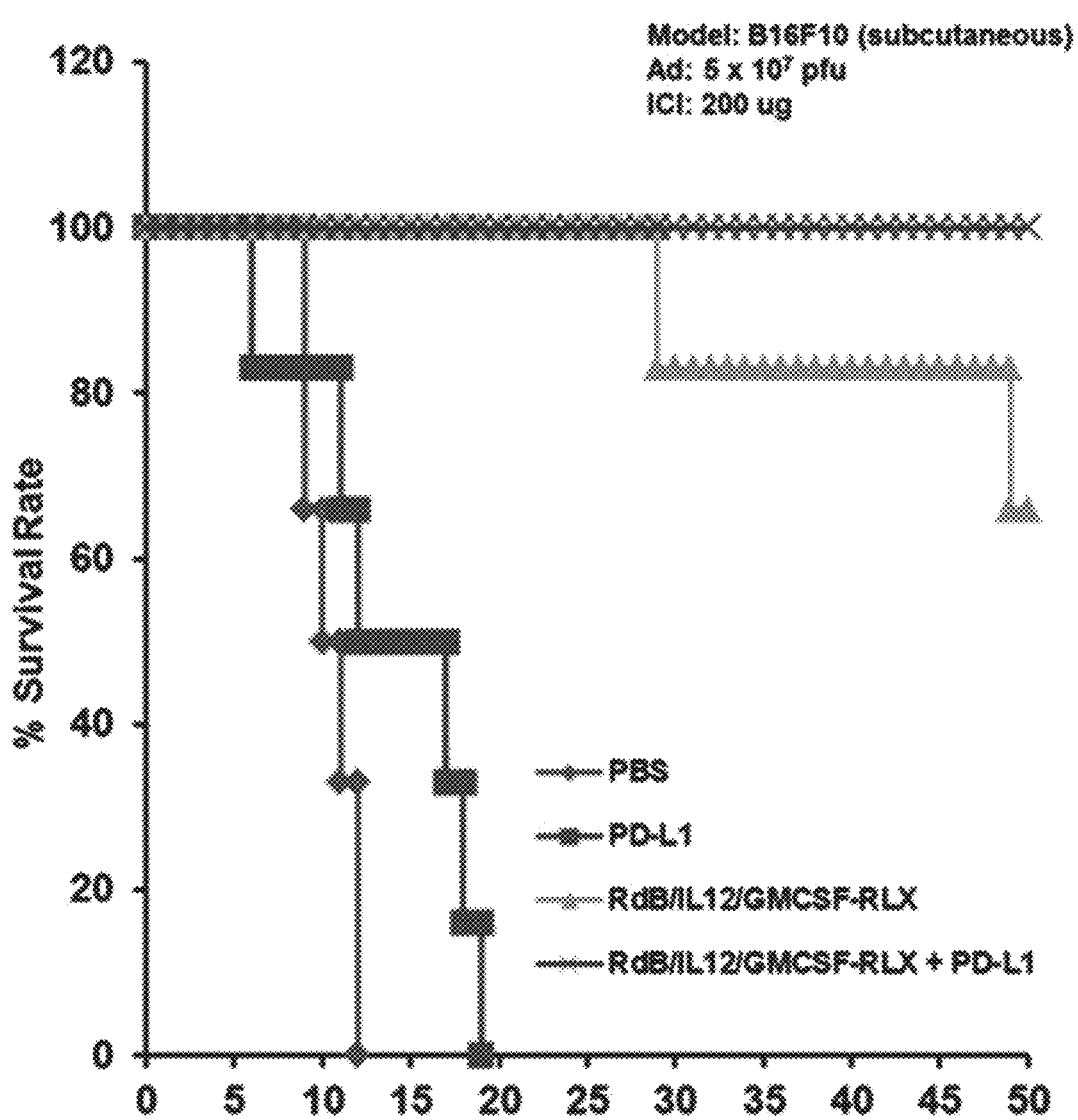

As a result, it was confirmed that in the control treated with PBS or the anti PD-L1 antibody, tumors had proliferated rapidly enough for the tumor volume to reach 3,000 mm3 or more on day 11 or 15, respectively, thereby exhibiting aggressive tumor growth, whereas in the group treated with RdB/IL12/shVEGF Ad or RdB/IL12/GMCSF-RLX Ad, as a result of comparison with the PBS-treated group on day 22, tumor growth was suppressed by 99.3% or 99.5% (FIGS. 3A and 4A), respectively. Furthermore, when the adenovirus and the anti PD-L1 antibody were co-administered (RdB/IL12/shVEGF Ad+PD-L1, RdB/IL12/GMCSF-RLX Ad+PD-L1), the tumor volume was more remarkably decreased than that of the group treated with the adenovirus or the anti PD-L1 antibody alone, in the same manner as described above. Although an anticancer effect similar to that of the group treated with the adenovirus alone (RdB/IL12/shVEGF Ad, RdB/IL12/GMCSF-RLX Ad) was exhibited until day 27, from the time when one month had passed, the growth of tumors was continuously suppressed in the group to which the anti PD-L1 antibody was co-administered, whereas in the group treated with the adenovirus alone, the growth of tumors was increased over time, so that a significant difference in tumor volume could be confirmed between the group treated with the adenovirus alone and the group to the adenovirus and the antibody were co-administered (FIGS. 3A and 4A). In addition, it could be seen that on day 50, in the control treated with PBS or the anti PD-L1 antibody, complete remission could not be confirmed, whereas in the RdB/IL12/shVEGF Ad or RdB/IL12/GMCSF-RLX Ad group, the survival rates were 66% (⅘) and 50% (⅗), respectively, and when the adenovirus and the anti PD-L1 antibody were co-administered, the survival rates were 66% (⅘) and 100% (6/6) which is complete remission. Furthermore, it was confirmed that all the mice in the RdB/IL12/shVEGF Ad+PD-L1 or RdB/IL12/GMCSF-RLX Ad+PD-L1 group survived until day 44 or day 50, respectively, whereas at the same time point, the RdB/IL12/shVEGF Ad or RdB/IL12/GMCSF-RLX Ad group exhibited a survival rate of 66% (⅘), and all the mice in the control were killed by tumors (FIGS. 3B and 4B). These results mean that the anticancer effect by treatment with the immune checkpoint inhibitor anti PD-L1 antibody alone was relatively insignificant, whereas RdB/IL12/shVEGF Ad or RdB/IL12/GMCSF-RLX Ad exhibited an excellent anticancer effect, and the anticancer effect of the recombinant adenovirus is further enhanced when co-administered with the anti PD-L1 antibody.

2. Anticancer Effect by Co-Administration with Immune Checkpoint Inhibitor

The present inventors compared the anticancer effects between only administration of the recombinant adenovirus and the co-administration of the recombinant adenovirus and the immune checkpoint inhibitor using the oncolytic adenovirus at a dose (1×109 VP) which is five times lower than that of the previous experiment using 5×109 VP, in order to evaluate the synergistic effect by the co-administration with the immune checkpoint inhibitor in more detail. Further, based on the results, when the anti PD-L1 antibody, the anti PD-1 antibody, or the anti CTLA-4 antibody was used as the immune checkpoint inhibitor, the anticancer effects of these antibodies were compared, and in the present experiment, RdB/IL12/GMCSF-RLX Ad was used as the recombinant adenovirus.

Figure 5:
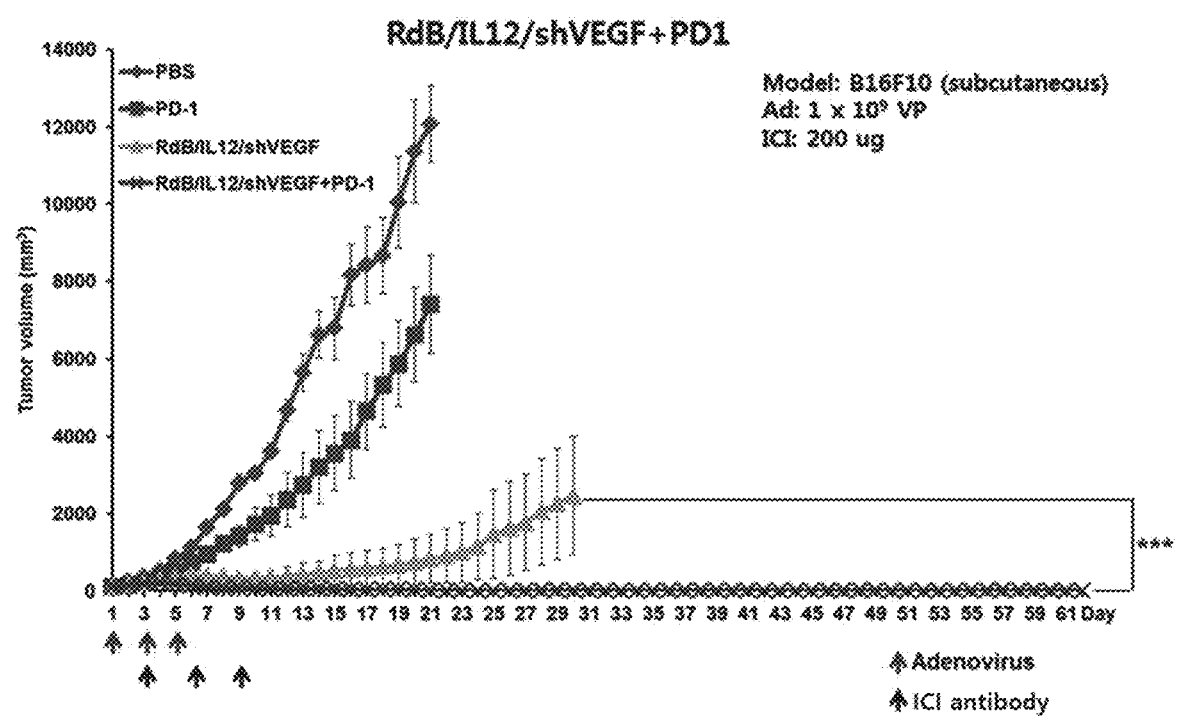
FIG. 5 confirms an anticancer effect according to the administration of RdB/IL12/shVEGF Ad and the co-administration of RdB/IL12/shVEGF Ad and an immune checkpoint inhibitor (anti PD-1 antibody) in mice with melanoma, and is a result confirming a change in volume of tumors when RdB/IL12/shVEGF Ad is administered at a relatively low dose of $1 \times 10^9$ VP.
Figure 6:
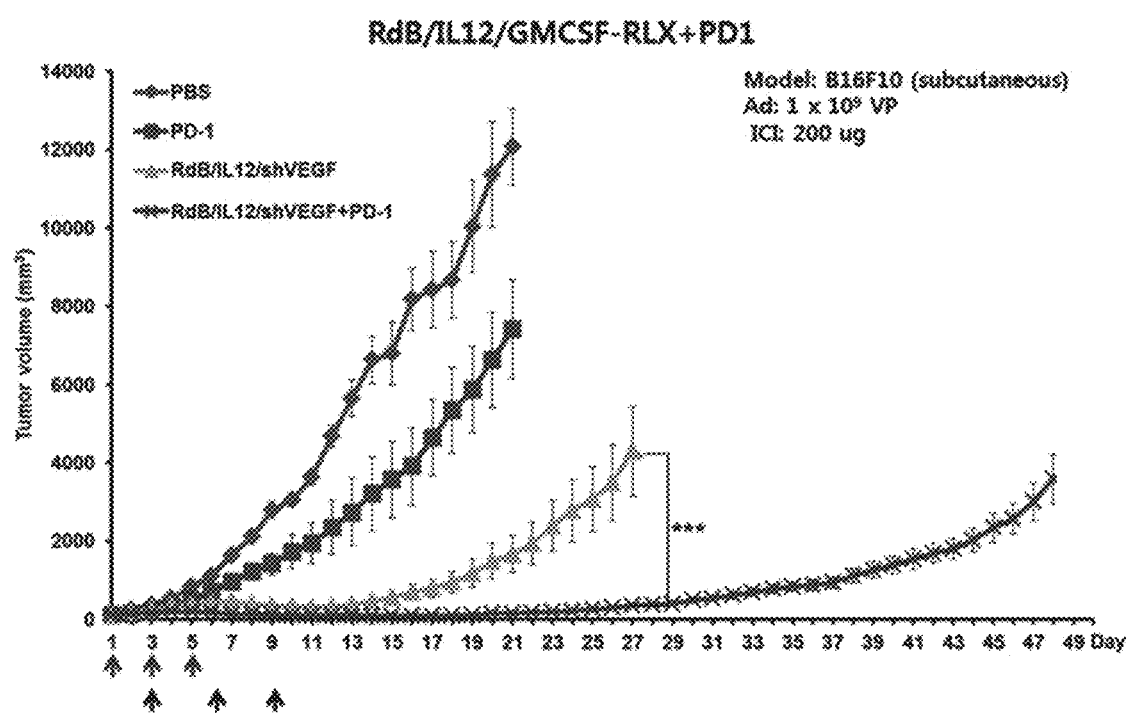
FIG. 6 confirms an anticancer effect according to the administration of RdB/IL12/GMCSF-RLX Ad and the co-administration of RdB/IL12/GMCSF-RLX Ad and an immune checkpoint inhibitor (anti PD-1 antibody) in mice with melanoma, and is a result confirming a change in volume of tumors when RdB/IL12/GMCSF-RLX Ad is administered at a relatively low dose of $1 \times 10^9$ VP.

As a result, on day 18, as a result of comparison with the tumor volume of the PBS-treated group, the tumor growth suppression rate of the RdB/IL12/shVEGF Ad group was 92.9%, but the tumor growth suppression rate was increased to 99.7% by the co-administration with the anti PD-1 antibody, and the tumor growth suppression rate of the RdB/IL12/GMCSF-RLX Ad group (90.1%) was also greatly increased to 98.9% by the co-administration with the anti PD-1 antibody (FIGS. 5 and 6). In addition, only 17% (⅙) of the RdB/IL12/shVEGF Ad group underwent complete remission, but in the RdB/IL12/shVEGF Ad+PD-1 group, the complete remission rate was 83% (⅚), which is greatly increased.

Figure 7:
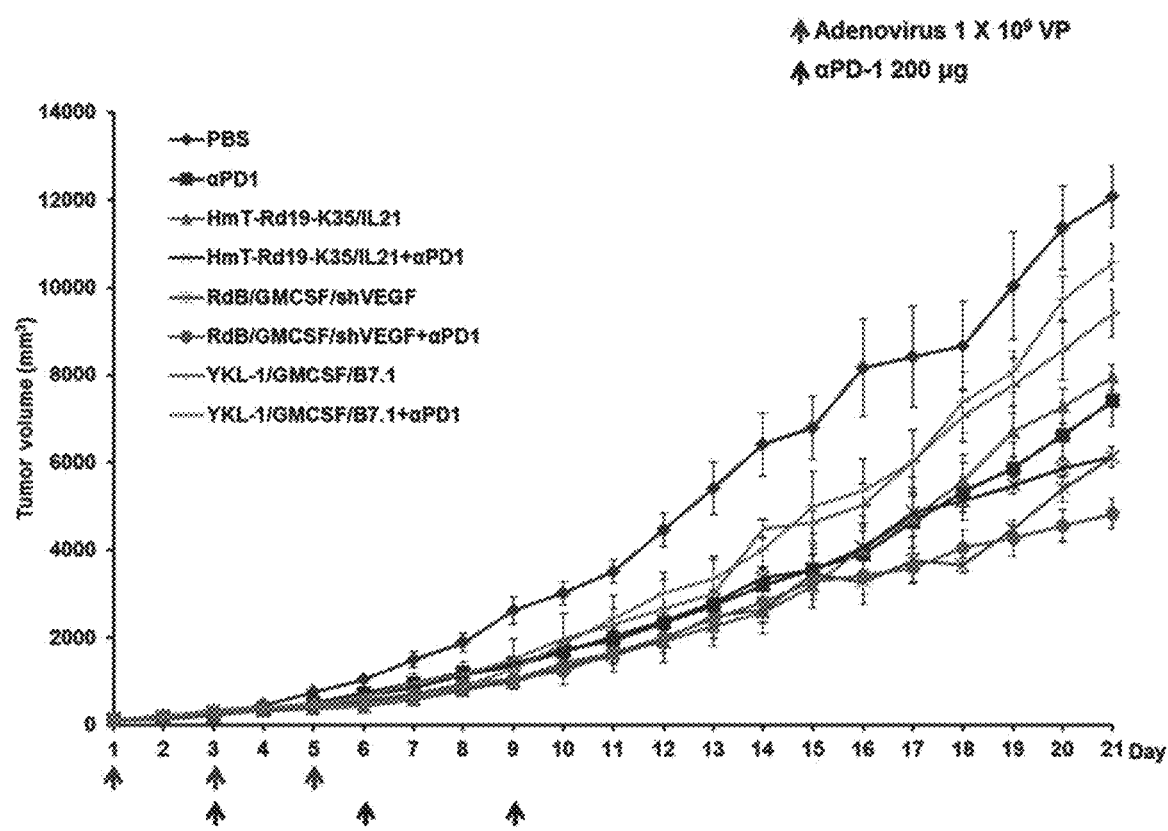
FIG. 7 is a result confirming an anticancer effect according to the co-administration of HmT-Rd19-K35/IL21 Ad, RdB/GMCSF/shVEGF Ad, and YKL-1/GMCSF/B7.1 Ad and an immune checkpoint inhibitor (anti PD-1 antibody) in mice with melanoma.

Meanwhile, in order to confirm whether other types of recombinant adenoviruses also exhibited the synergistic effect by the co-administration with the immune checkpoint inhibitor, HmT-Rd19-K35/IL21 Ad, RdB/GMCSF/shVEGF Ad, or YKL-1/GMCSF/B7.1 Ad and the anti PD-1 antibody were co-administered, and then the anticancer effects thereof were confirmed. As a result, as illustrated in FIG. 7, the fact was that in most of the recombinant adenoviruses, the tumor volume was decreased to some degree through the co-administration of the anti PD-1 antibody, but most of the recombinant adenoviruses failed to exhibit a remarkable effect as much as the recombinant adenovirus of the present invention (RdB/IL12/shVEGF Ad, RdB/IL12/GMCSF-RLX Ad) did, and in particular, the effect of YKL-1/GMCSF/B7.1 Ad on the whole was not excellent as compared to that of the group treated with the anti PD-1 antibody alone. From these results, it can be seen that the synergistic effect by the co-administration with the immune checkpoint inhibitor is not applicable to all recombinant adenoviruses, and is a unique effect of the recombinant adenovirus of the present invention.

Figure 8A:
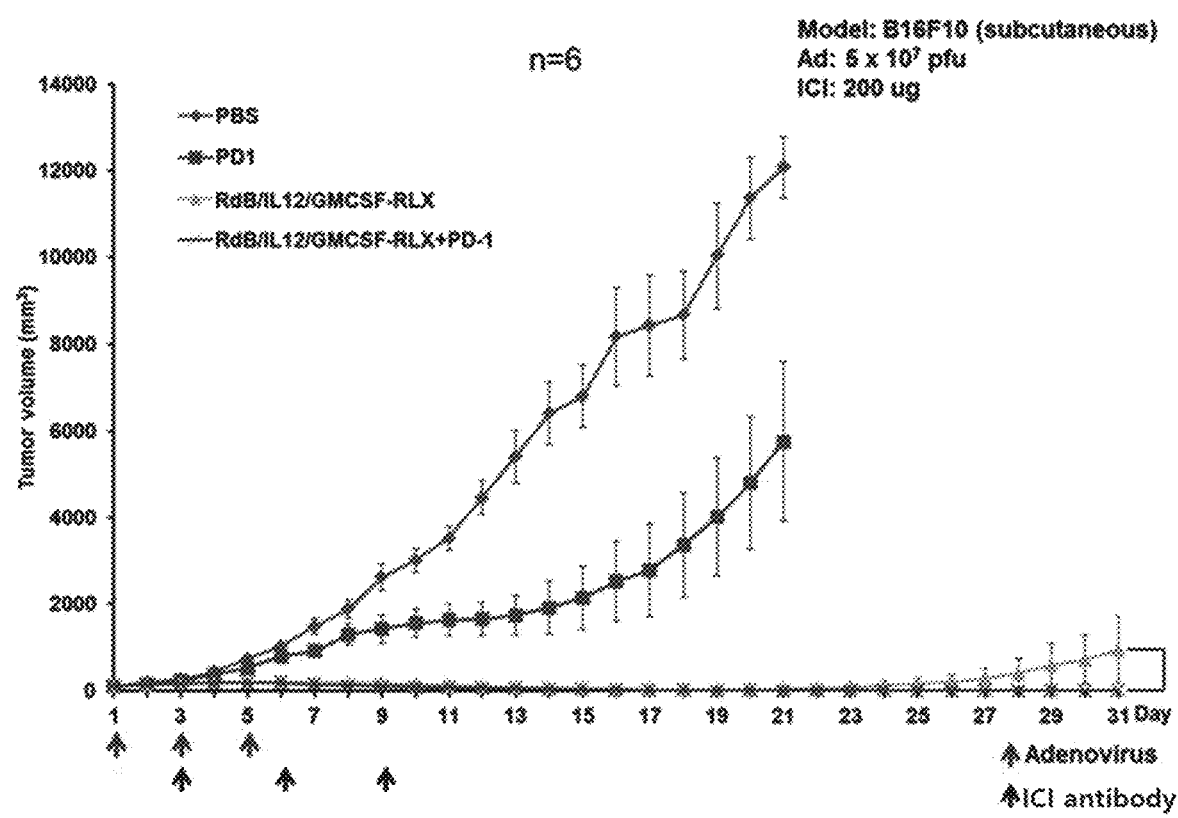
FIGS. 8A and 8B confirm an anticancer effect according to the administration of RdB/IL12/GMCSF-RLX Ad and the co-administration of RdB/IL12/GMCSF-RLX Ad and an immune checkpoint inhibitor (anti PD-1 antibody) in mice with melanoma.
Figure 8B:
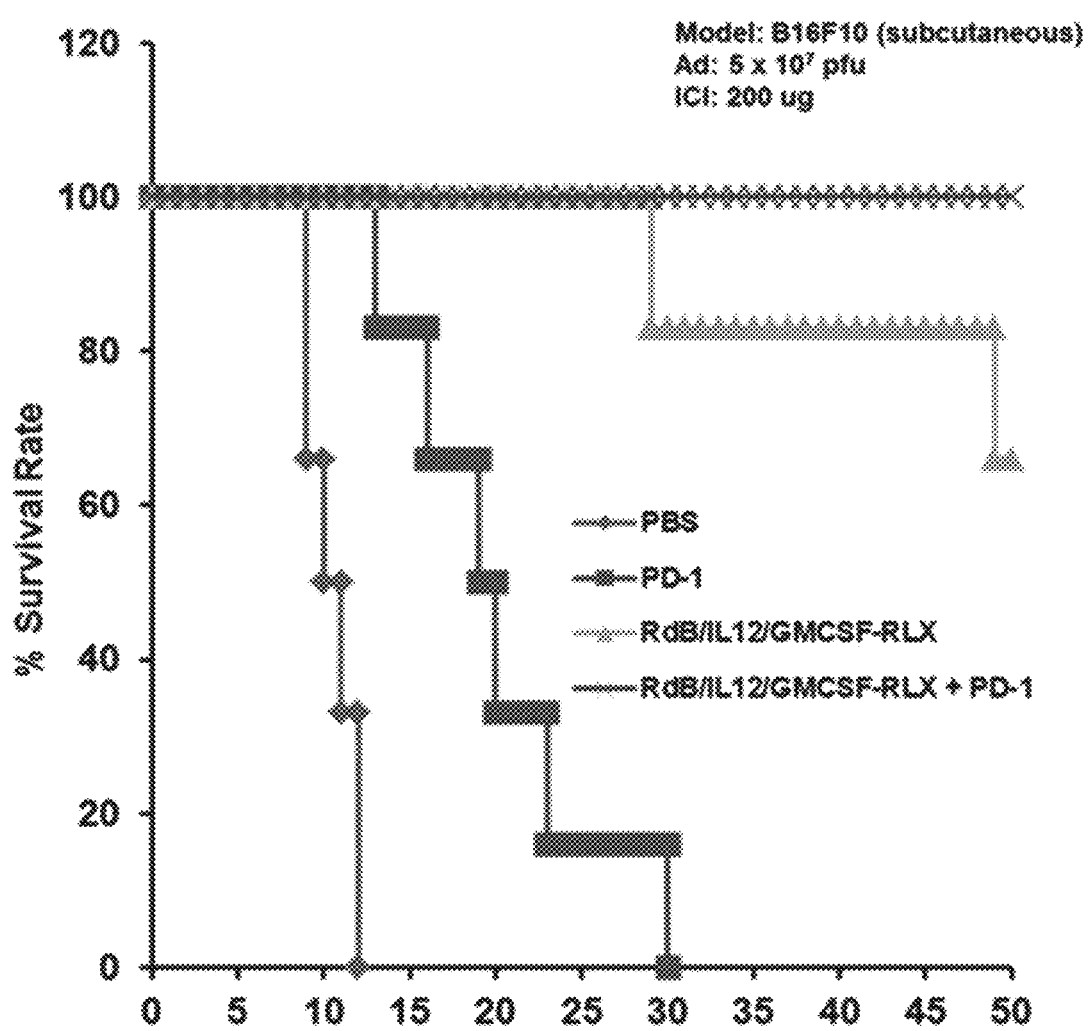
Figure 9A:
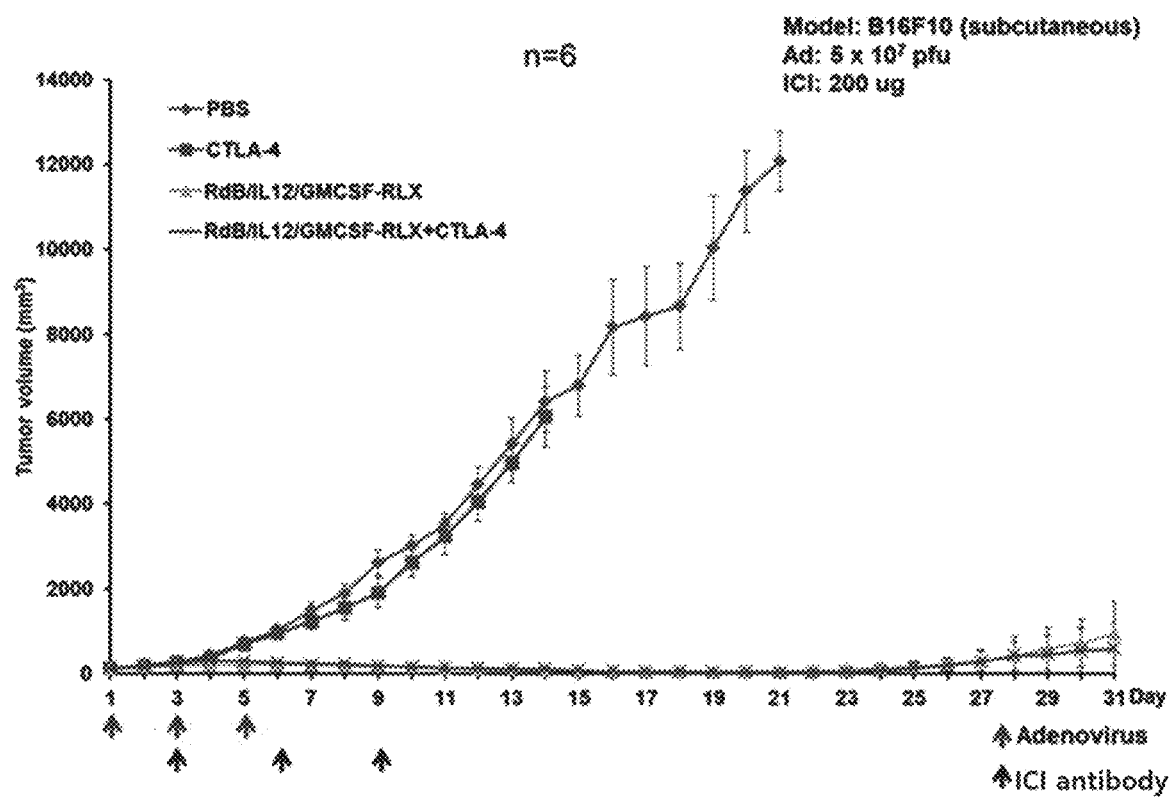
FIGS. 9A and 9B confirm an anticancer effect according to the administration of RdB/IL12/GMCSF-RLX Ad and the co-administration of RdB/IL12/GMCSF-RLX Ad and an immune checkpoint inhibitor (anti CTLA-4 antibody) in mice with melanoma.
Figure 9B:
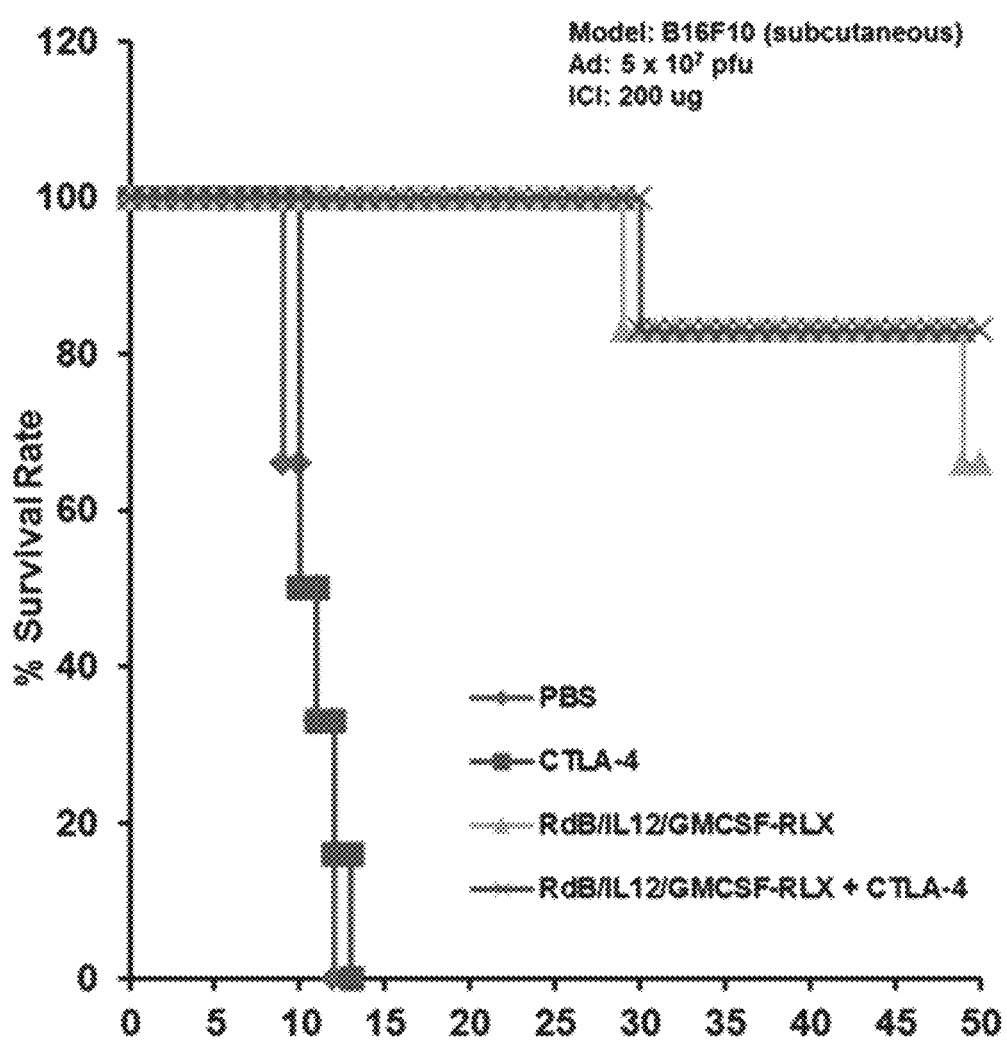

Further, it was confirmed that as a result of confirming the anticancer effect by the type of immune checkpoint inhibitor, the control mice treated with PBS, the anti PD-L1 antibody, the anti PD-1 antibody, or the anti CTLA-4 antibody had proliferated rapidly enough for the tumor volume to reach 3,000 mm3 or more on day 11, 15, 18, or 11, respectively, thereby exhibiting aggressive tumor growth, whereas in the case of the groups treated with RdB/IL12/GMCSF-RLX Ad+anti PD-L1 antibody, RdB/IL12/GMCSF-RLX Ad+anti PD-1 antibody, and RdB/IL12/GMCSF-RLX Ad+anti CTLA-4 antibody, on day 21, as a result of comparison with the PBS-treated group, tumor growth was greatly suppressed by 99.9%, 99.9%, or 99.2%, respectively (FIGS. 4A, 8A, and 9A). In addition, on day 50, in the RdB/IL12/GMCSF-RLX Ad group, the complete remission rate was 50% (3/6), whereas when the anti PD-L1 antibody, the anti PD-1 antibody, or the anti CTLA-4 antibody was co-administered, the complete remission rate was 100% (6/6), 83% (5/6), and 83% (5/6), respectively, which are increased. Furthermore, mice treated with RdB/IL12/GMCSF-RLX Ad+anti PD-L1 antibody, RdB/IL12/GMCSF-RLX Ad+anti PD-1 antibody, and RdB/IL12/GMCSF-RLX Ad+anti CTLA-4 antibody survived until day 50, day 50, or day 30, respectively, whereas at the same time points, the RdB/IL12/GMCSF-RLX Ad group exhibited a survival rate of 66% (4/6), 66 (4/6), and 83% (5/6), respectively (FIGS. 4B, 8B, and 9B). These results show that even when not only the anti PD-L1 antibody, but also the anti PD-1 antibody, or the anti CTLA-4 antibody are used, the anticancer effect of the recombinant adenovirus is enhanced, however, it could be seen that when the anti PD-L1 antibody or the anti PD-L1 antibody was co-administered, the anticancer effect-associated synergistic effect of RdB/IL12/GMCSF-RLX Ad was more predominant than that when the anti CTLA-4 antibody was co-administered.

3. Confirmation of Immune Memory Effect Against Recurrent Cancer

The present inventors intended to confirm an immune memory effect and an anticancer effect against a recurrent cancer according to the recombinant adenovirus of the present invention, or the co-administration of the recombinant adenovirus and the immune checkpoint inhibitor by comparing the volume of secondary tumors injected into melanoma mice, and the like.

Figure 10A:
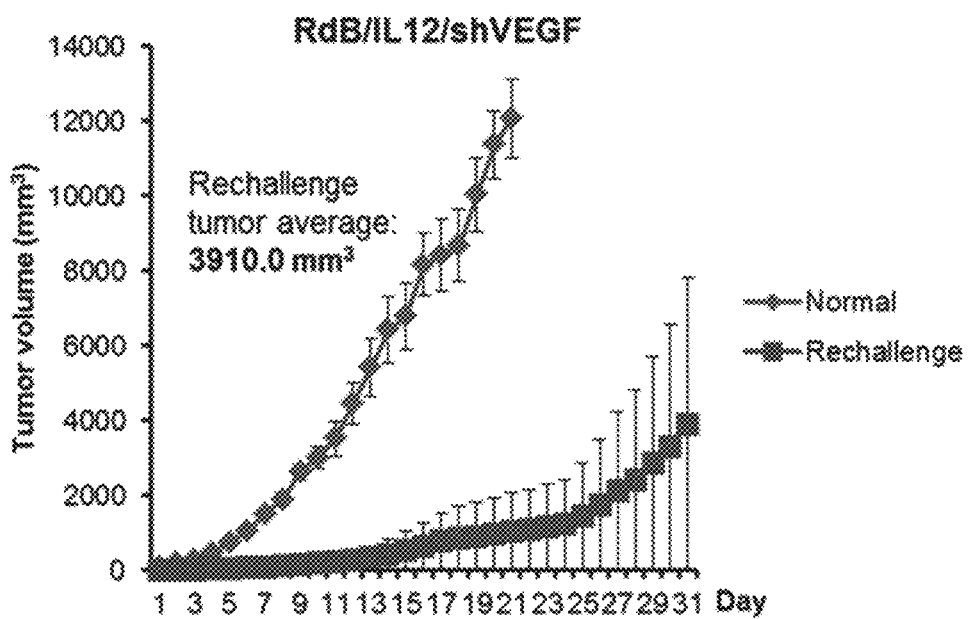
FIGS. 10A and 10B confirm an anti-tumor immune memory effect according to the administration of RdB/IL12/shVEGF and the co-administration of RdB/IL12/shVEGF Ad and an immune checkpoint inhibitor (anti PD-L1 antibody) in mice with melanoma.
Figure 10B:
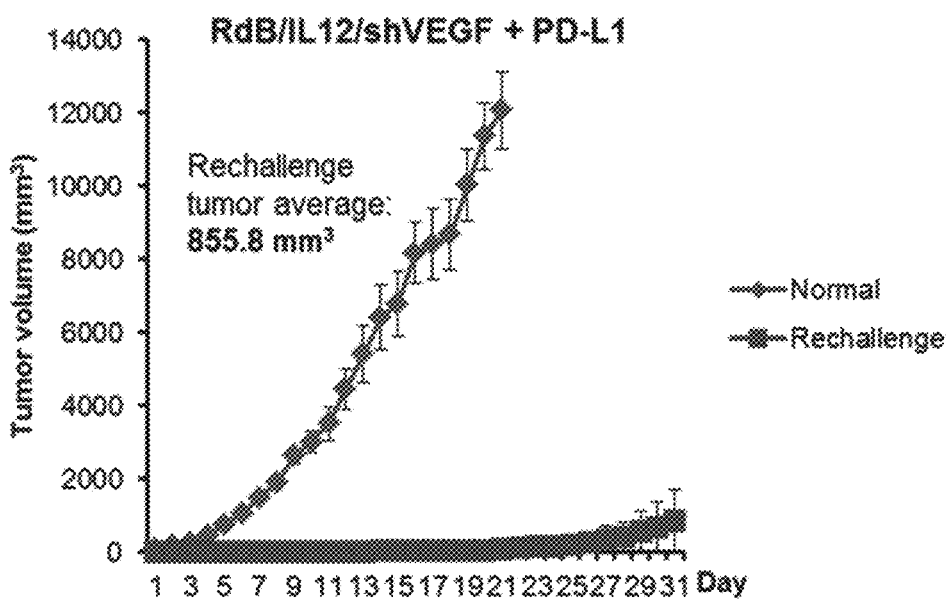

As a result, it could be confirmed that in the RdB/IL12/shVEGF Ad group, the growth of secondary tumors was markedly inhibited (FIG. 10A), and particularly, the growth of secondary tumors was more remarkably inhibited by the co-administration with the immune checkpoint inhibitor anti PD-1 antibody (FIG. 10B). These results mean that the recombinant adenovirus of the present invention may prevent the recurrence of tumors in advance through the effect of enhancing the anti-tumor immune response by immune memory, suggesting that the effect may be enhanced by the co-administration with the immune checkpoint inhibitor as with the above-described anticancer effect.

4. Verification of Anticancer Effect of RdB/IL12/GMCSF-RLX Ad (1) Confirmation of Expression Patterns of IL-12, GM-CSF, and Relaxin In order to verify the anticancer effect according to the co-expression of IL-12, GM-CSF, and relaxin (RLX) genes, RdB/IL12/GMCSF-RLX Ad, which is an adenovirus in which the IL-12 gene was inserted into the E1 region of an adenovirus and GM-CSF and relaxin genes were inserted into the E3 region of the adenovirus, was manufactured as described above. The RdB/IL12/GMCSF-RLX Ad is a cancer cell-specific oncolytic adenovirus in which an E1B gene as an initial gene of an adenovirus was deleted and an E1A gene was modified, and the expression level of IL-12, GM-CSF, or RLX by the manufactured adenovirus was confirmed. Specifically, a Syrian hamster pancreatic cancer cell line (Hap-T1) was infected with RdB/IL12/GMCSF-RLX at a multiplicity of infection (MOI) of 0.2, 0.5, 1, 2, and 5, and 48 hours later, the media thereof were collected. Thereafter, the expression levels of IL-12 and GM-CSF were confirmed through enzyme-linked immunosorbent assay (ELISA), and the expression level of relaxin was confirmed through a reverse transcription polymerase chain reaction (RT-PCR).

Figure 11:
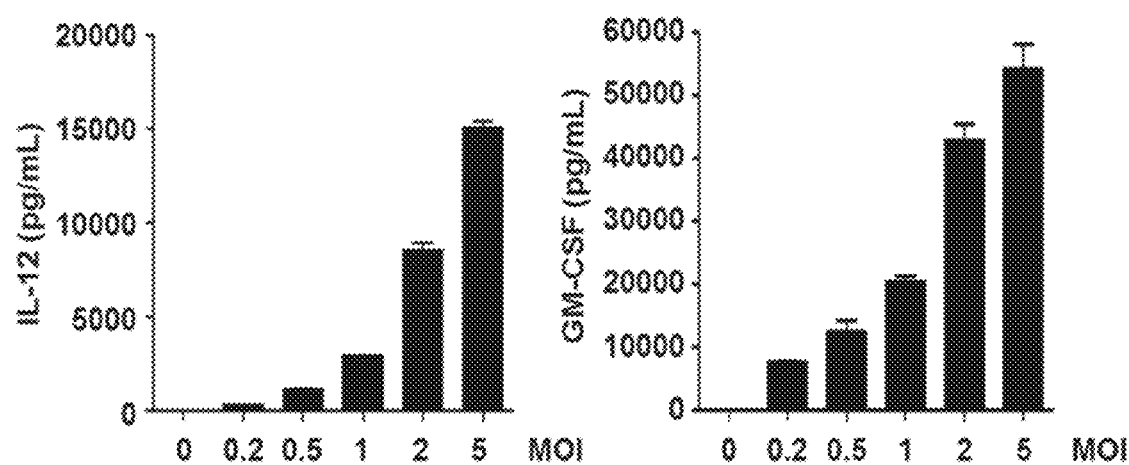
FIG. 11 is a result confirming, through enzyme-linked immunosorbent assay (ELISA), a change in expression of IL-12 and GMCSF according to multiplicity of infection (MOI) after a Syrian hamster pancreatic cancer cell line (Hap-T1) is infected with RdB/IL12/GMCSF-RLX Ad.
Figure 12:
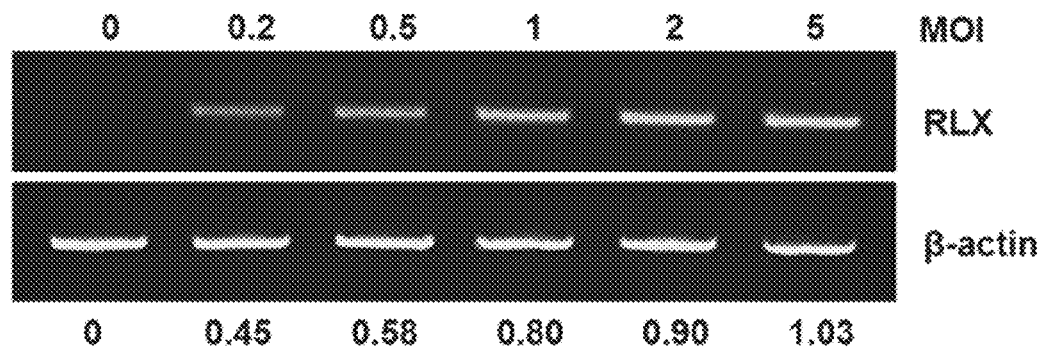
FIG. 12 is a result confirming, through reverse transcription polymerase chain reaction (RT-PCR), a change in expression of relaxin according to MOI after a Syrian hamster pancreatic cancer cell line (Hap-T1) is infected with RdB/IL12/GMCSF-RLX Ad.

As a result, as illustrated in FIGS. 11 and 12, the expression level of IL-12, GM-CSF, or relaxin was increased dependently on the MOI of the adenovirus, so that the co-expression of the genes could be experimentally confirmed.

(2) Enhancement of Anticancer Effect by Co-Administration with αPD-1 in Syrian Hamster Tumor Animal Model In order to verify the enhancement of the anticancer effect by the co-administration of RdB/IL12/GMCSF-RLX Ad and αPD-1, $7 \times 10^7$ viral particles (VP)/30 μl of RdB/IL12/GMCSF-RLX Ad was administered intratumorally to a Syrian hamster tumor animal model induced by subcutaneously injecting a HaP-T1 pancreatic cancer cell line, and along with this, 10 mg/kg of αPD-1 was administered intraperitoneally, and then the resulting change in volume of tumors was observed. Meanwhile, an RdB/IL12/GMCSF-RLX Ad only administration group was used as a comparative group.

Figure 13:
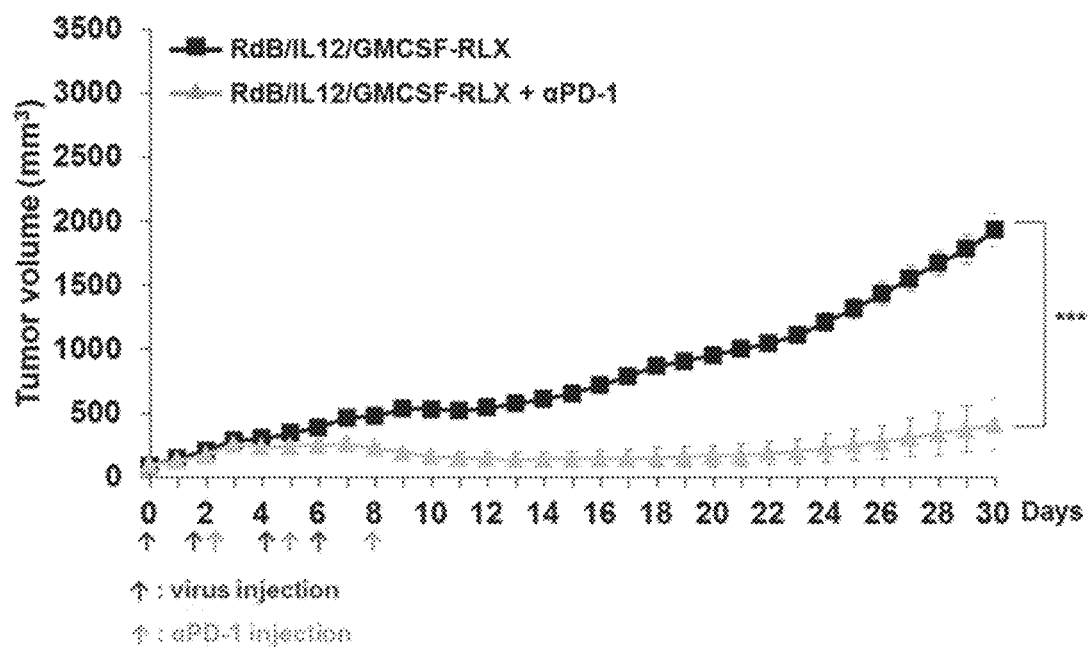
FIG. 13 is a result confirming a change in volume of tumors according to the co-administration of RdB/IL12/GMCSF-RLX Ad and an immune checkpoint inhibitor (anti PD-1 antibody) in a Syrian hamster tumor animal model.

As a result, as illustrated in FIG. 13, in the tumor tissue to which RdB/IL12/GMCSF-RLX Ad was administered alone, tumors grew continuously, so that on day 30 after the first administration of the virus, the tumor volume reached 1.982±126 mm3, whereas in the co-administration group of RdB/IL12/GMCSF-RLX Ad and αPD-1, the growth of tumors was suppressed until day 30 after the first administration of the virus, thereby suppressing the growth of tumors to a level of about 79% as compared to the single administration group. Further, in the co-administration group of RdB/IL12/GMCSF-RLX Ad and αPD-1, the complete remission rate of tumors was about 50%, but in the RdB/IL12/GMCSF-RLX Ad only administration group, the complete remission was not observed at all (not illustrated). That is, these results suggest that the anticancer therapeutic efficacy of RdB/IL12/GMCSF-RLX Ad is remarkably improved by the co-administration with αPD-1.

(3) Change in Tumor Tissue by Co-Administration with αPD-1 in Syrian Hamster Tumor Animal Model In order to specifically confirm the change in tumor tissues by the co-administration of RdB/IL12/GMCSF-RLX Ad and αPD-1, after $7 \times 10^7$ VP of RdB/IL12/GMCSF-RLX Ad and 10 mg/kg of αPD-1 were co-administered as described above, the collected tumor tissues were immunohistologically evaluated. Meanwhile, an αPD-1 or RdB/IL12/GMCSF-RLX Ad only administration group and a PBS administration group were used as a comparative group and a control, respectively.

Figure 14:
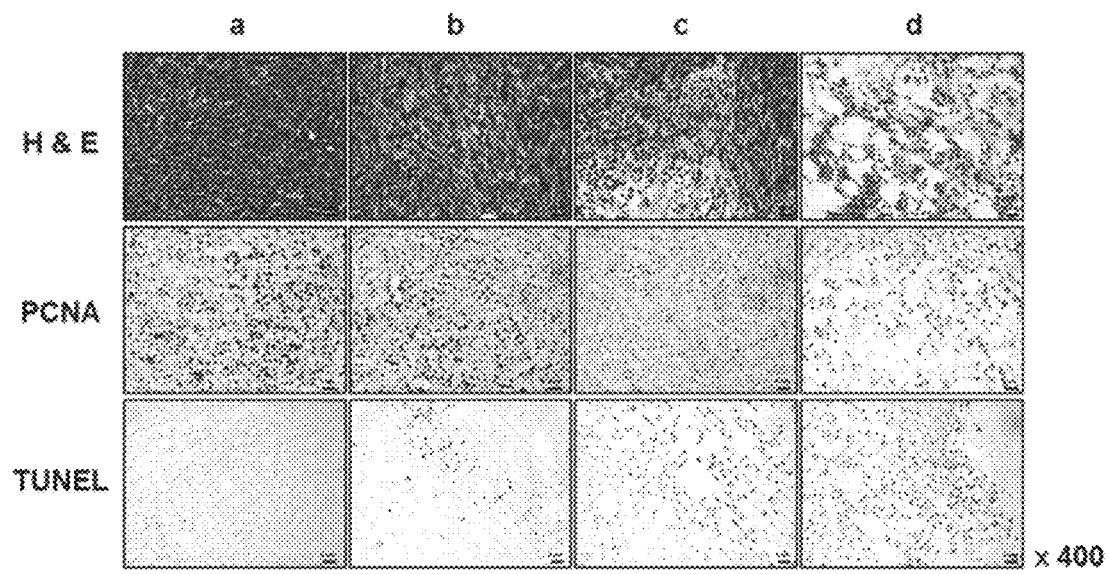
FIG. 14 is a result confirming, by an immunohistological method, a change in tumor tissues according to the co-administration of RdB/IL12/GMCSF-RLX Ad and an immune checkpoint inhibitor (anti PD-1 antibody) in a Syrian hamster tumor animal model.

As a result, as illustrated in FIG. 14, it could be confirmed that in the tumor tissue to which PBS was administered, a necrosis site was hardly confirmed, whereas most of the tumor tissues to which RdB/IL12/GMCSF-RLX Ad and αPD-1 were co-administered became necrotic. Further, the effect by the co-administration, that is, the remarkably low proliferation of tumor cells (PCNA) and the increased cell necrosis (TUNEL) were very remarkable as compared to the case where αPD-1 or RdB/IL12/GMCSF-RLX Ad was administered alone.

(4) Change in Expression of Cell Populations and IFN-γ in Tumor Tissues by Co-Administration with αPD-1

Figure 15:
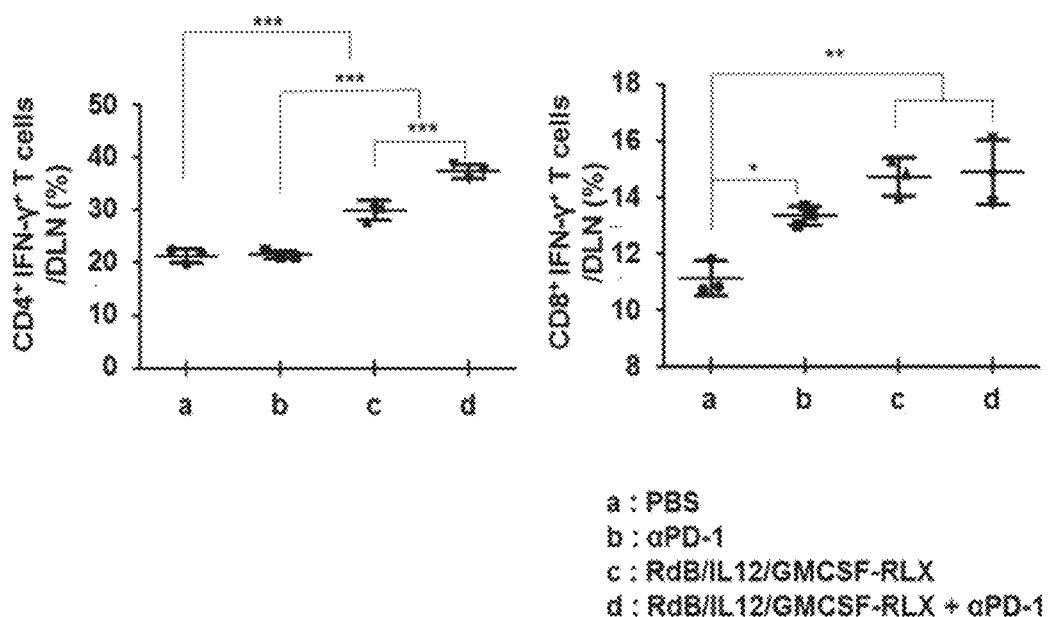
FIG. 15 is a result confirming a change in population of interferon (IFN)-γ-expressing CD4$^+$ or CD8$^+$ T cells according to the co-administration of RdB/IL12/GMCSF-RLX Ad and an immune checkpoint inhibitor (anti PD-1 antibody) in a draining lymph node (DLN).
Figure 16:
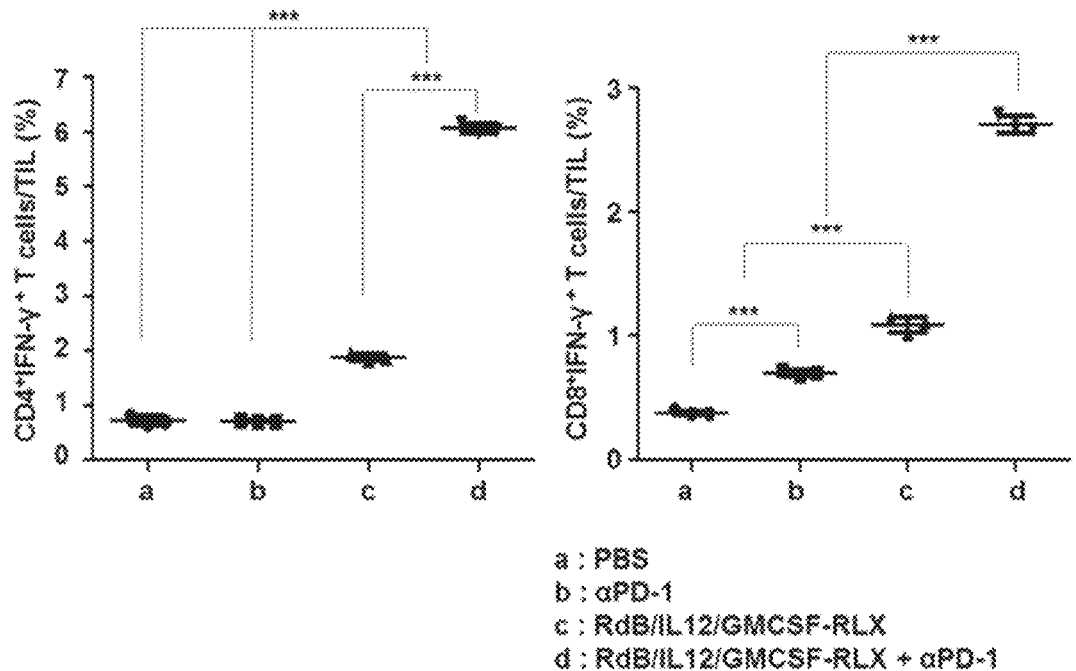
FIG. 16 is a result confirming a change in population of interferon (IFN)-γ-expressing CD4$^+$ or CD8$^+$ T cells according to the co-administration of RdB/IL12/GMCSF-RLX Ad and an immune checkpoint inhibitor (anti PD-1 antibody) in lymphocytes infiltrated into tumor tissues.

In order to evaluate whether the infiltration and activation of T cells in tumor tissues could be induced as the infiltration of αPD-1 in tumor tissues was increased by RdB/IL12/GMCSF-RLX Ad, a change in population of interferon (IFN)-γ-expressing CD4+ or CD8+ T cells was evaluated in the infiltrated lymphocytes in the draining lymph node (DLN) and tumor tissues. As a result, as illustrated in FIGS. 15 and 16, in the RdB/IL12/GMCSF-RLX Ad or αPD-1 only administration group and the co-administration group of RdB/IL12/GMCSF-RLX Ad and αPD-1, the population of IFN-γ-expressing CD4+ and CD8+ T cells was observed at a high level as compared to the PBS or αPD-1 only administration group (P<0.001 or P<0.01). In particular, it could be confirmed that in the co-administration group of RdB/IL12/GMCSF-RLX Ad and αPD-1, the population of IFN-γ-expressing CD4+ and CD8+ T cells was also significantly increased as compared to the group to which RdB/IL12/GMCSF-RLX Ad or αPD-1 was administered alone (P<0.001), and this result indicates that the co-administration of RdB/IL12/GMCSF-RLX Ad and αPD-1 induces the infiltration and activation of interferon (IFN)-γ-expressing CD4+ or CD8+ T cells in tumors.

Figure 17:
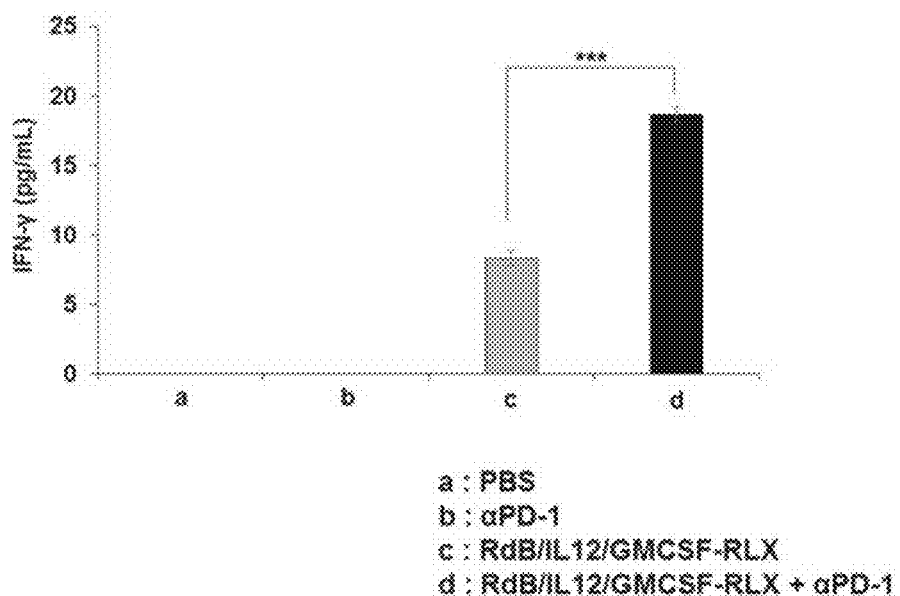
FIG. 17 is a result confirming a change in expression of IFN-γ in tumor tissues according to the co-administration of RdB/IL12/GMCSF-RLX Ad and an immune checkpoint inhibitor (anti PD-1 antibody).

In addition, in order to evaluate the expression level of IFN-γ in the tumor tissue to which the adenovirus was administered, tumor tissues were extracted from mice to which the adenovirus and the like were administered and finely ground, and then an IFN-γ ELISA analysis was carried out. As a result, as illustrated in FIG. 17, it could be confirmed that when PBS or αPD-1 was administered intratumorally alone, IFN-γ was not detected at all, and in the RdB/IL12/GMCSF-RLX Ad only administration group, only 8.3 pg/mg of IFN-γ per 1 g of the tumor tissue was detected, whereas in the co-administration group of RdB/IL12/GMCSF-RLX Ad and αPD-1, 18.7 pg/mg of IFN-γ per 1 g of the tumor tissue was detected. That is, it was revealed that the aforementioned co-administration increased the activity of immune cells by increasing the expression of IFN-γ in tumors, and ultimately, contributed to the enhancement of the anticancer effect.

(5) Confirmation of Anticancer Effect Under Condition of Resistance to Immune Checkpoint Inhibitor In order to evaluate whether the co-administration of RdB/IL12/GMCSF-RLX Ad and αPD-1 could exhibit effective therapeutic efficacy under a condition of resistance to the immune checkpoint inhibitor, the effect of the co-administration to tumors pre-treated with αPD-1 on suppression of the growth of tumors was evaluated. Specifically, when the growth of tumors was not effectively suppressed by the administration of αPD-1 alone (on day 9 after the first treatment of the antibody), RdB/IL12/GMCSF-RLX Ad was administered four times in total at an interval of 2 days. Meanwhile, an αPD-1 only administration group was used as a comparative group.

Figure 18:
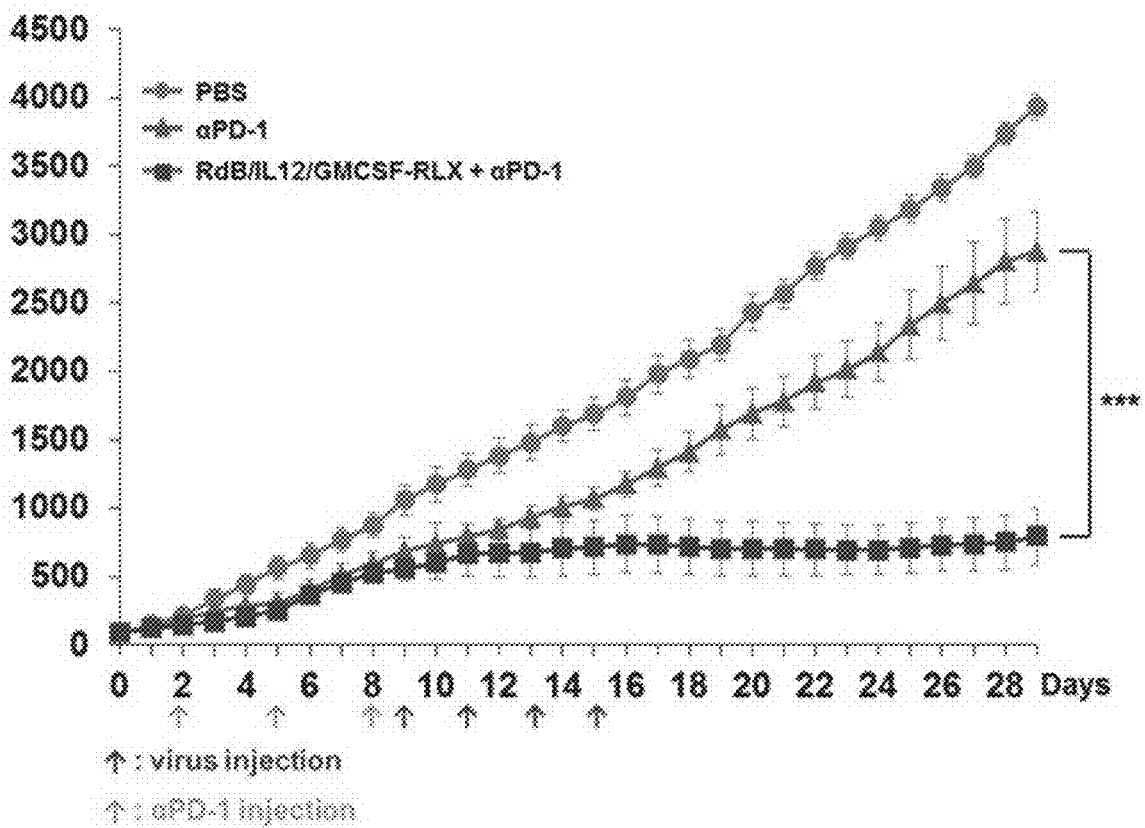
FIG. 18 is a result confirming a change in volume of tumors according to the co-administration of RdB/IL12/GMCSF-RLX Ad and an immune checkpoint inhibitor (anti PD-1 antibody) under a condition of resistance to the immune checkpoint inhibitor.
Figure 19:
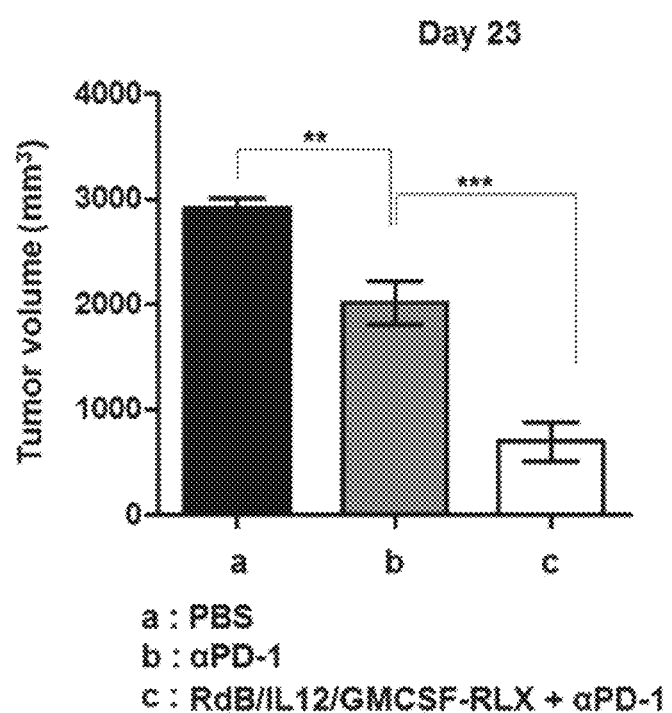
FIG. 19 is a result confirming a change in volume of tumors on day 23 after administration according to the co-administration of RdB/IL12/GMCSF-RLX Ad and an immune checkpoint inhibitor (anti PD-1 antibody) under a condition of resistance to the immune checkpoint inhibitor.

As a result, as illustrated in FIG. 18, the administration of RdB/IL12/GMCSF-RLX Ad initiated when the tumor volume reached 915±78 mm3 effectively suppressed the growth of tumors for 10 days from the first day of the administration. Interestingly, the αPD-1 only administration group exhibited a rapid increase in tumor growth rate, and thus failed to suppress the growth of tumors, whereas the co-administration group continuously suppressed the growth of tumors even during the aforementioned period. Further, as a result of comparing a change in tumor volume (on day 23 after the administration), the effect of suppressing the growth in the co-administration group was the most remarkable. That is, the aforementioned co-administration exhibited effective anticancer therapeutic efficacy even under a condition of resistance to the immune checkpoint inhibitor. Accordingly, it is suggested that the aforementioned co-administration may become a therapy beneficial to a patient having tolerance to an immune checkpoint inhibitor single therapy.

Figure 20:
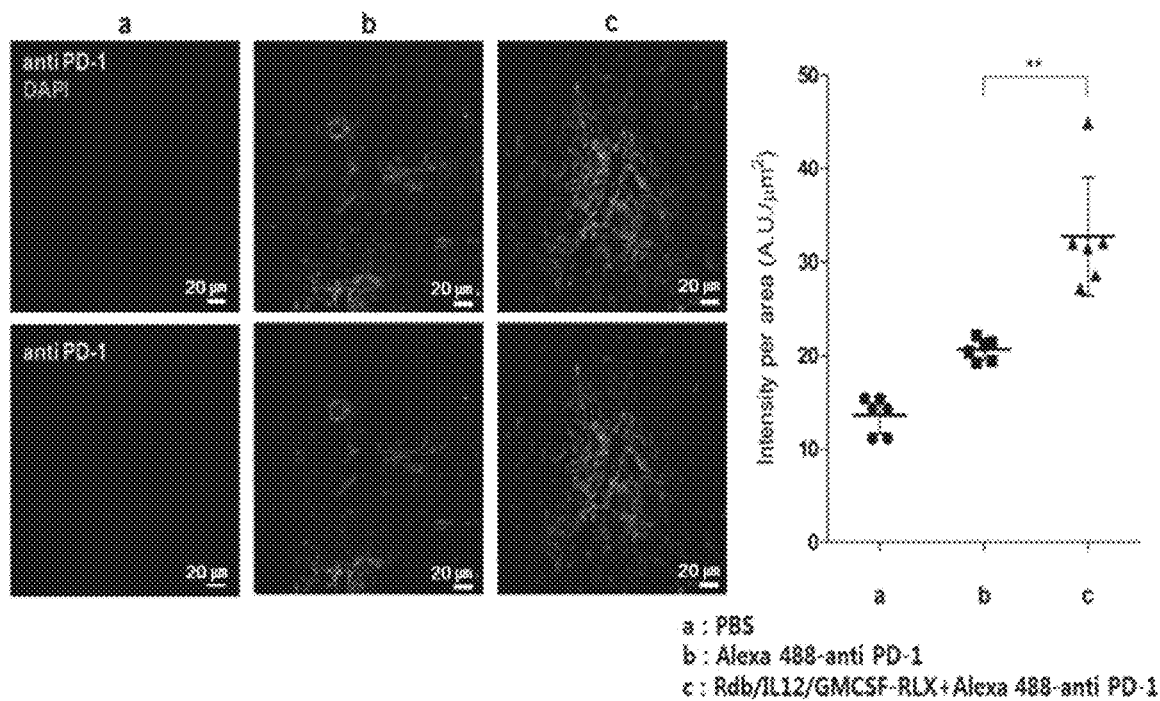
FIG. 20 confirms a change in infiltration of an immune checkpoint inhibitor (anti PD-1 antibody) in tumor tissues by the administration of RdB/IL12/GMCSF-RLX Ad, and is a result of quantifying the accumulation of Alexa 488-αPD-1 in tumor tissues through an immunofluorescence analysis.
Figure 21:
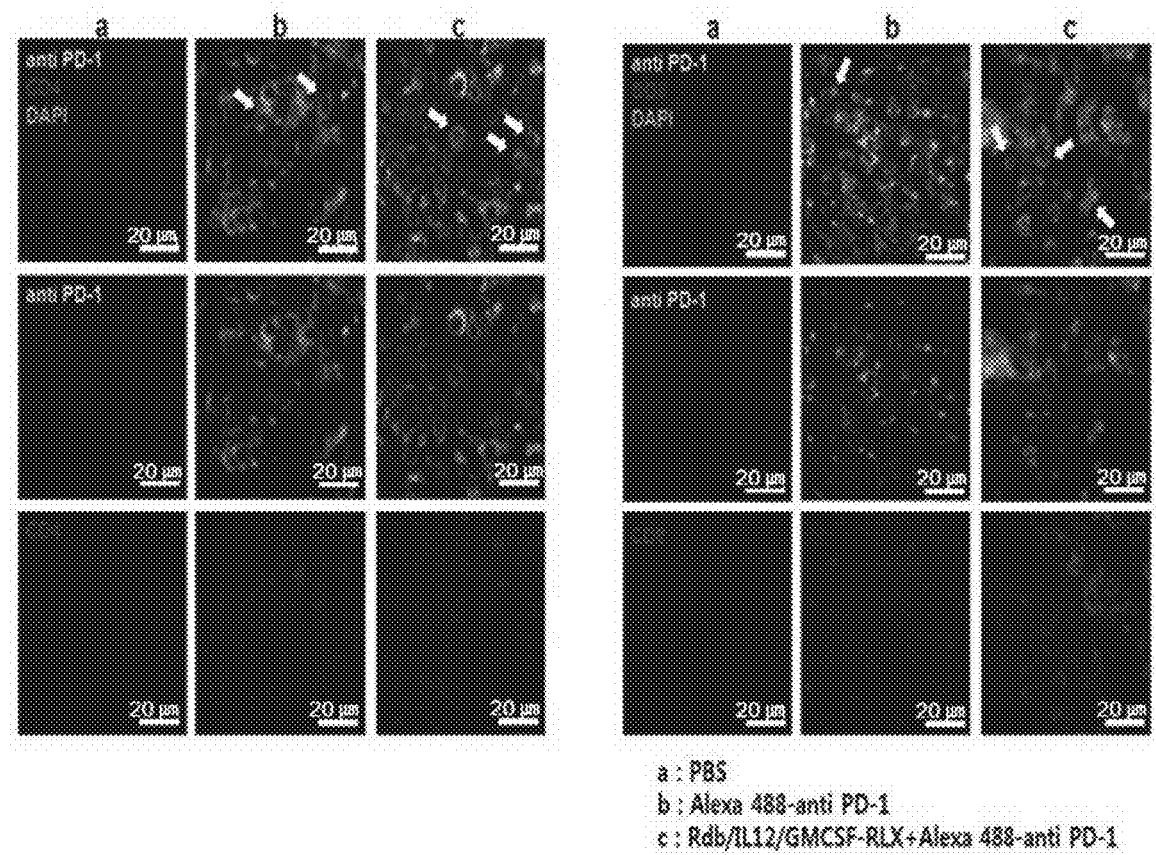
FIG. 21 confirms a change in infiltration of an immune checkpoint inhibitor (anti PD-1 antibody) in tumor tissues by the administration of RdB/IL12/GMCSF-RLX Ad, and is a result confirming whether Alexa 488-αPD-1 is located in an expression site of CD4+ or CD8+ T cells through immunofluorescence.

(6) Change in Infiltration of αPD-1 into Tumor Tissues by Administration of RdB/IL12/GMCSF-RLX Ad It was predicted that the expression of RLX in tumor tissues would exhibit synergistic anticancer therapeutic efficacy by promoting the intratumoral infiltration of αPD-1. Accordingly, it was intended to evaluate whether RdB/IL12/GMCSF-RLX Ad increased the intratumoral infiltration of αPD-1 into a desmoplastic pancreatic tumor tissue. RdB/IL12/GMCSF-RLX Ad was directly administered to tumor tissues on day 0 or day 2, αPD-1 was administered intraperitoneally on day 2 (c: RdB/IL12/GMCSF-RLX+Alexa 488-anti PD-1), and an Alexa 488-conjugated αPD-1 only administration group (b; Alexa 488-anti PD-1) and a PBS only administration group (a; PBS) were used as a comparative group and a control, respectively. The tumor tissue treated as described above was collected on day 7, and the accumulation of Alexa 488-αPD-1 in the tumor tissue was quantified through an immunofluorescence analysis. As a result of quantifying the accumulation of Alexa 488-αPD-1 per tissue area, as illustrated in FIG. 20, the PBS only administration group or αPD-1 only administration group exhibited 14±2 A.U./μm2 or 21±1 A.U./μm2, respectively, whereas the co-administration group exhibited 32±6 A.U./μm2. From the result, it could be seen that RdB/IL12/GMCSF-RLX Ad remarkably improved the infiltration of αPD-1 into tumor tissues and contributed to the improvement of localization of αPD-1 in tumor tissues. Furthermore, in order to confirm whether the Alexa 488-αPD-1 was located at the expression site of CD4+ or CD8+ T cells, with respect to each tumor tissue to which PBS (a: PBS) or Alexa 488-conjugated αPD-1 (b: Alexa 488-anti PD-1) are administered alone or RdB/IL12/GMCSF-RLX Ad and Alexa 488-conjugated αPD-1 were co-administered (c: RdB/IL12/GMCSF-RLX+Alexa 488-anti PD-1), immunostaining was carried out on CD4+CD8+. As a result, as illustrated in FIG. 21, in the co-administration group, the co-localization of αPD-1 and CD4+ or CD8+ T cells were observed at a higher level than in the Alexa 488-αPD-1 only administration group.

Figure 22:
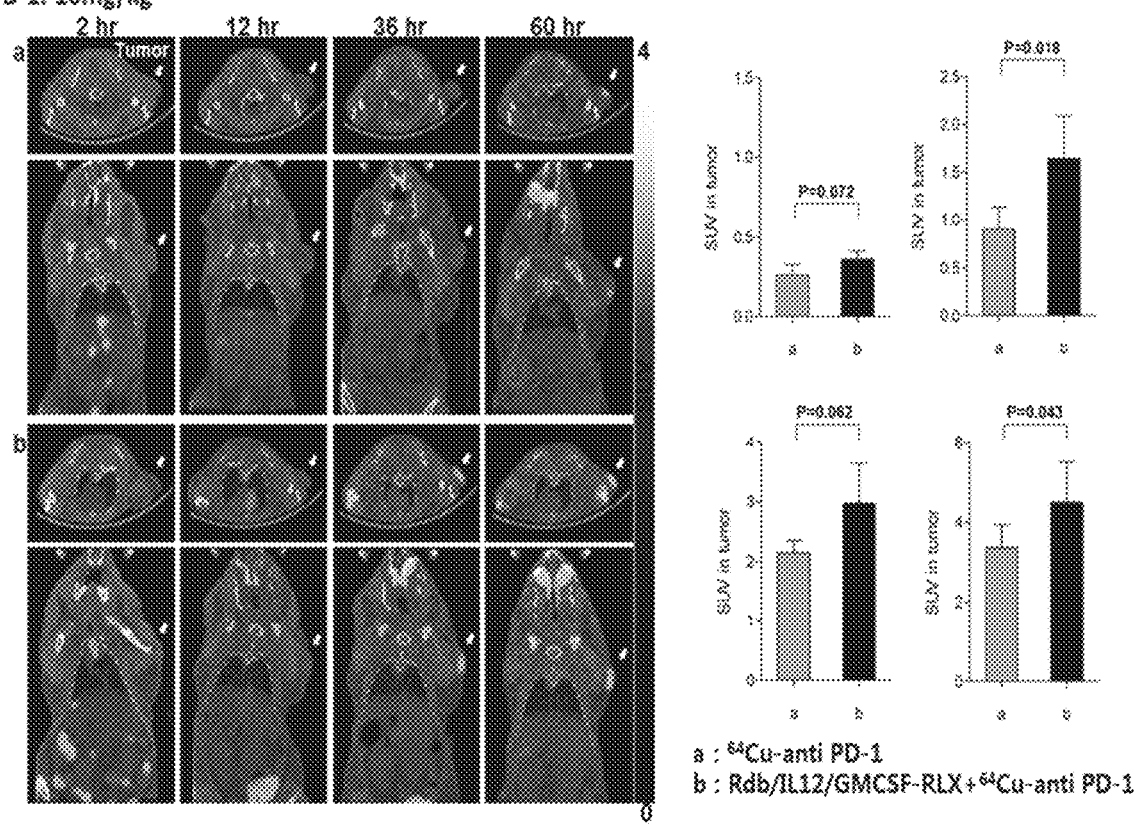
FIG. 22 confirms a change in infiltration of an immune checkpoint inhibitor (anti PD-1 antibody) by the administration of RdB/IL12/GMCSF-RLX Ad on a systemic basis, and is a result of analyzing an immune positron emission tomography (PET) image over time.
Figure 23:
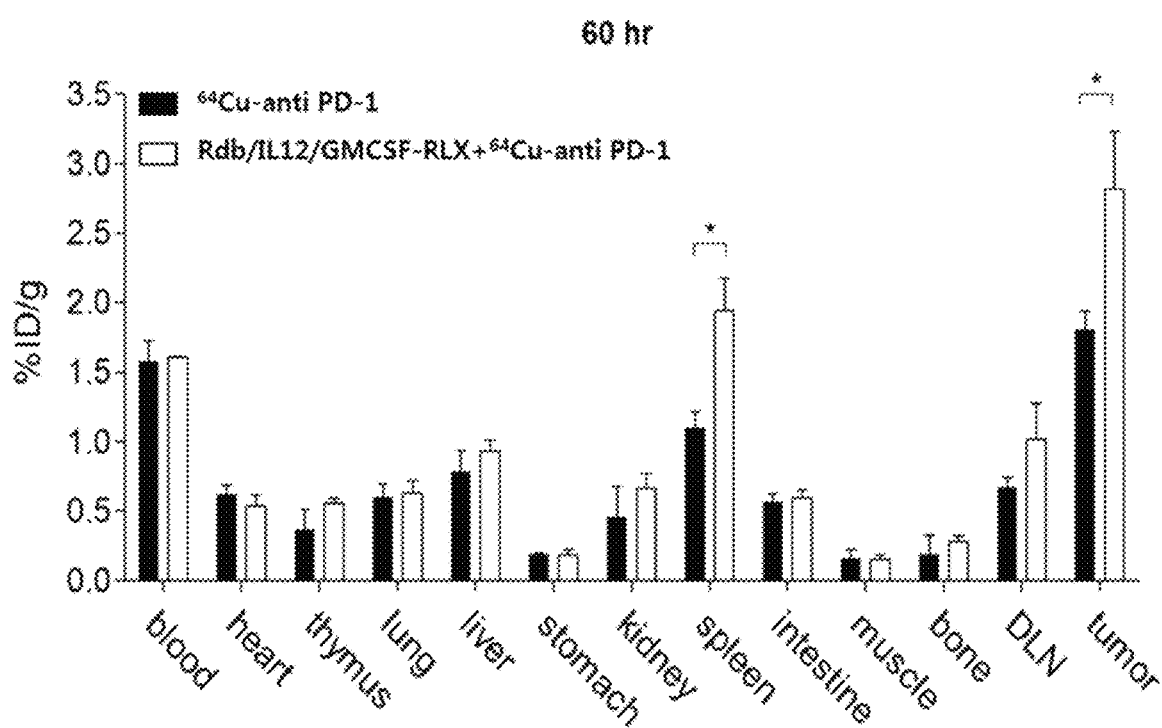
FIG. 23 confirms a change in infiltration of an immune checkpoint inhibitor (anti PD-1 antibody) by the administration of RdB/IL12/GMCSF-RLX Ad on a systemic basis, and is a result of evaluating and comparing the distribution or absorption of $^{64}$CU-αPD-1 in various tissues including tumor tissues by % ID/g.

In order to evaluate the intratumoral infiltration of αPD-1 for the whole body, 64Cu-αPD-1 in which αPD-1 and 64Cu were conjugated was administered along with RdB/IL12/GMCSF-RLX Ad to HaP-Ti-transplanted hamsters using 1,4,7,10-tetraazacyclododecane-1,4,7,10-tetraacetic acid by the above-described method, thereby obtaining an immuno-PET image. PET scanning was carried out at 2, 12, 36, and 60 hours after the administration of 64Cu-αPD-1, and main PET imaging was carried out along with CT for anatomical description. A 64Cu-αPD-1 only administration group was used as a comparative group. As a result, as illustrated in FIG. 22, the intratumoral absorption of 64Cu-αPD-1 by the co-administration group and the single administration group calculated as an SUV was as follows: 0.26±0.06 and 0.36±0.05 (P=0.072) at 2 hours; 0.90±0.22 and 1.68±0.45 (P=0.018) at 12 hours; 2.14±0.19 and 2.97±0.67 (P=0.062) at 36 hours; and 3.37±0.57 and 4.50±1.02 (P=0.043) at 60 hours. That is, it was observed that at all the aforementioned time points, the intratumoral absorption of 64Cu-αPD-1 by the co-administration group was significantly higher than that by the 64Cu-αPD-1 only administration group. Further, the distribution or absorption of 64Cu-αPD-1 in various tissues including tumor tissues was calculated as % ID/g at 60 hours after the administration of 64Cu-αPD-1. As a result, as illustrated in FIG. 23, it could be confirmed that the absorption exhibited by the single administration group and the co-administration group was: 1.80±0.13% ID/g, 2.80±0.41% ID/g (P<0.05), respectively in tumor tissues; and 1.10±0.11% ID/g, 1.94±0.23% ID/g (P<0.05), respectively in the spleen, and in the co-administration group, the absorption of 64Cu-αPD-1 was improved in both tumor tissues and the spleen. Furthermore, in addition to these tissues, the draining lymph node (DLN) known as a T cell-enriched site was enlarged by infection with RdB/IL12/GMCSF-RLX Ad (result not illustrated). That is, when the aforementioned experimental results are taken together, it could be seen that the infection with RdB/IL12/GMCSF-RLX Ad remodeled or decomposed the extracellular matrix in tumor tissues and improved the absorption of αPD-1 in tumor tissues by the enhanced immune response by IL-12 and GM-CSF, and as a result, a synergistic effect of the co-administration occurred.

The above-described description of the present invention is provided for illustrative purposes, and the person skilled in the art to which the present invention pertains will understand that the present invention can be easily modified into other specific forms without changing the technical spirit or essential features of the present invention. Therefore, it should be understood that the above-described Examples are illustrative only in all aspects and are not restrictive.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A recombinant adenovirus comprising: a gene encoding Interleukin 12 (IL-12); a gene encoding a granulocyte-macrophage colony-stimulating factor (GM-CSF); and a gene encoding relaxin.

2. The recombinant adenovirus of claim 1, wherein the recombinant adenovirus has any one or more regions selected from the group consisting of E1 and E3 regions deleted.

3. The recombinant adenovirus of claim 2, wherein in the recombinant adenovirus a gene encoding IL-12 is inserted into the E1 region, and a gene encoding GM-CSF and a gene encoding relaxin are inserted into the E3 region.

4. A pharmaceutical composition for preventing or treating cancer, the composition comprising: (a) the recombinant adenovirus of claim 1; and (b) a pharmaceutically acceptable carrier.

5. The pharmaceutical composition of claim 4, wherein the composition further comprises immune checkpoint inhibitors.

6. The pharmaceutical composition of claim 5, wherein the immune checkpoint inhibitor is any one selected from the group consisting of a programmed cell death-1 (PD-1) antagonist, a programmed cell death-ligand 1 (PD-L1) antagonist, a programmed cell death-ligand 2 (PD-L2) antagonist, a cluster of differentiation 27 (CD27) antagonist, a cluster of differentiation 28 (CD28) antagonist, a cluster of differentiation 70 (CD70) antagonist, a cluster of differentiation 80 (CD80, also known as B7-1) antagonist, a cluster of differentiation 86 (CD86, also known as B7-2) antagonist, a cluster of differentiation 137 (CD137) antagonist, a cluster of differentiation 276 (CD276) antagonist, a killer-cell immunoglobulin-like receptors (KIRs) antagonist, a lymphocyte-activation gene 3 (LAG3) antagonist, a tumor necrosis factor receptor superfamily, member 4 (TNFRSF4, also known as CD134) antagonist, a glucocorticoid-induced TNFR-related protein (GITR) antagonist, a glucocorticoid-induced TNFR-related protein ligand (GITRL) antagonist, a 4-1BB ligand (4-1BBL) antagonist, a cytolytic T lymphocyte associated antigen-4 (CTLA-4) antagonist, an adenosine A2A receptor (A2AR) antagonist, a V-set domain-containing T-cell activation inhibitor 1 (VTCN1) antagonist, a B- and T-lymphocyte attenuator (BTLA) antagonist, an indoleamine 2,3-dioxygenase (IDO) antagonist, a T-cell Immunoglobulin domain and Mucin domain 3 (TIM-3) antagonist, a V-domain Ig suppressor of T cell activation (VISTA) antagonist, a killer cell lectin-like receptor subfamily A (KLRA) antagonist, and a combination thereof.

7. The pharmaceutical composition of claim 4, wherein the cancer is any one selected from the group consisting of gastric cancer, lung cancer, non-small cell lung cancer, breast cancer, ovarian cancer, liver cancer, bronchial cancer, nasopharyngeal cancer, laryngeal cancer, pancreatic cancer, bladder cancer, colon cancer, cervical cancer, bone cancer, non-small cell bone cancer, hematologic malignancy, skin cancer, head or neck cancer, uterine cancer, colorectal cancer, anal near cancer, colon cancer, fallopian tube cancer, endometrial cancer, vaginal cancer, vulva cancer, Hodgkin's disease, esophageal cancer, small intestine cancer, endocrine cancer, thyroid cancer, parathyroid cancer, adrenal cancer, soft tissue sarcoma, urethral cancer, penile cancer, prostate cancer, chronic or acute leukemia, lymphocytic lymphoma, kidney or hydroureter cancer, renal cell carcinoma, renal pelvic carcinoma, salivary gland cancer, sarcoma cancer, pseudomyxoma peritonei, hepatoblastoma, testicular cancer, glioblastoma, cheilocarcinoma, ovarian germ cell tumors, basal cell carcinoma, multiple myeloma, gallbladder cancer, choroidal melanoma, cancer of the ampulla of Vater, peritoneal cancer, tongue cancer, small cell cancer, pediatric lymphoma, neuroblastoma, duodenal cancer, ureteral cancer, astrocytoma, meningioma, renal pelvis cancer, pudendum cancer, thymus cancer, central nervous system (CNS) tumors, primary central nervous system lymphoma, spinal cord tumors, brain stem neuroglioma, and pituitary adenoma.

8. The pharmaceutical composition of claim 4, wherein the cancer is a recurrent cancer.

9. The pharmaceutical composition of claim 4, wherein the composition enhances anti-tumor immunity.

10. A method for treating cancer comprising administering a composition comprising the recombinant adenovirus of claim 1; and a pharmaceutically acceptable carrier, to an individual.

11. The method according to claim 10, wherein the composition is administrated simultaneously, separately, or sequentially in combination with an immune checkpoint inhibitor.

* * * * *

SEQUENCE LISTING

<160> NUMBER OF SEQ ID NOS: 18

<210> SEQ ID NO 1
<211> LENGTH: 648
<212> TYPE: DNA
<213> ORGANISM: Mus musculus

<400> SEQUENCE: 1

```
atgtgtcaat cacgctacct cctcttttg gccaccttg ccctcctaaa ccacctcagt      60
ttggccaggg tcattccagt ctctggacct gccaggtgtc ttagccagtc ccgaaacctg     120
ctgaagacca cagatgacat ggtgaagacg gccagagaaa aactgaaaca ttattcctgc     180
actgctgaag acatcgatca tgaagacatc acacgggacc aaaccagcac attgaagacc     240
tgtttaccac tggaactaca caagaacgag agttgcctgg ctactagaga gacttcttcc     300
acaacaagag ggagctgcct gcccccacag aagacgtctt tgatgatgac cctgtgcctt     360
ggtagcatct atgaggactt gaagatgtac cagacagagt tccaggccat caacgcagca     420
cttcagaatc acaaccatca gcagatcatt ctagacaagg gcatgctggt ggccatcgat     480
gagctgatgc agtctctgaa tcataatggc gagactctgc gccagaaacc tctgtggga      540 gaagcagacc cttacagagt gaaaatgaag ctctgcatcc tgcttcacgc cttcagcacc     600
cgcgtcgtga ccatcaacag ggtgatgggc tatctgagct ccgcctga                 648
```

<210> SEQ ID NO 2
<211> LENGTH: 1008
<212> TYPE: DNA
<213> ORGANISM: Mus musculus

<400> SEQUENCE: 2

```
atgtgtcctc agaagctaac catctcctgg tttgccatcg ttttgctggt gtctccactc      60
atggccatgt gggagctgga gaaagacgtt tatgttgtag aggtggactg gactcccgat     120
gcccctggag aaacagtgaa cctcacctgt gacacgcctg aagaagatga catcacctgg     180
acctcagacc agagacatgg agtcataggc tctggaaaga ccctgaccat cactgtcaaa     240
gagtttctag atgctggcca gtacacctgc cacaaaggag gcgagactct gagccactca     300
catctgctgc tccacaagaa ggaaaatgga atttggtcca ctgaatttttt aaaaaatttc     360 aaaaacaaga ctttcctgaa gtgtgaagca ccaaattact ccggacggtt cacgtgctca     420
```

```
tggctggtgc aaagaaacat ggacttgaag ttcaacatca agagcagtag cagttcccct      480
gactctcggg cagtgacatg tggaatggcg tctctgtctg cagagaaggt cacactggac      540
caaagggact atgagaagta ttcagtgtcc tgccaggagg atgtcacctg cccaactgcc      600
gaggagaccc tgcccattga actggcgttg gaagcacggc agcagaataa atatgagaac      660
tacagcacca gcttcttcat cagggacatc atcaaaccag acccgcccaa gaacttgcag      720
atgaagcctt tgaagaactc acaggtggag gtcagctggg agtaccctga ctcctggagc      780
actccccatt cctacttctc cctcaagttc tttgttcgaa tccagcgcaa gaaagaaaag      840
atgaaggaga cagaggaggg gtgtaaccag aaaggtgcgt tcctcgtaga aagacatct       900 accgaagtcc aatgcaaagg cgggaatgtc tgcgtgcaag ctcaggatcg ctattacaat      960
tcctcatgca gcaagtgggc atgtgttccc tgcagggtcc gatcctag                1008

<210> SEQ ID NO 3
<211> LENGTH: 597
<212> TYPE: DNA
<213> ORGANISM: Artificial
<220> FEATURE:
<223> OTHER INFORMATION: IRES

<400> SEQUENCE: 3
tagcgatccg cccctctccc tcccccccc ctaacgttac tggccgaagc cgcttggaat        60
aaggccggtg tgcgtttgtc tatatgttat tttccaccat attgccgtct tttggcaatg     120
tgagggcccg gaaacctggc cctgtcttct tgacgagcat tcctaggggt cttcccctc      180 tcgccaaagg aatgcaaggt ctgttgaatg tcgtgaagga agcagttcct ctggaagctt     240
cttgaagaca acaacgtctg tagcgaccct tttgcaggca gcggaacccc ccacctggcg     300
acaggtgcct ctgcggccaa aagccacgtg tataagatac acctgcaaag gcggcacaac     360
cccagtgcca cgttgtgagt tggatagttg tggaaagagt caaatggctc tcctcaagcg     420
tattcaacaa ggggctgaag gatgcccaga aggtacccca ttgtatggga tctgatctgg    480
ggcctcggta cacatgcttt acatgtgttt agtcgaggtt aaaaaaacgt ctaggccccc    540
gaaccacggg gacgtggttt ccttttgaa aaacacgatg ataatatggc cacaacc         597

<210> SEQ ID NO 4
<211> LENGTH: 426
<212> TYPE: DNA
<213> ORGANISM: Mus musculus

<400> SEQUENCE: 4
atgtggctgc agaatttact tttcctgggc attgtggtct acagcctctc agcacccacc       60
cgctcaccca tcactgtcac ccggccttgg aagcatgtag aggccatcaa agaagccctg     120
aacctcctgg atgacatgcc tgtcacattg aatgaagagg tagaagtcgt ctctaacgag     180
ttctccttca agaagctaac atgtgtgcag accgcctga agatattcga gcagggtcta     240
cggggcaatt tcaccaaact caagggcgcc ttgaacatga cagccagcta ctaccagaca     300
tactgccccc caactccgga aacggactgt gaaacacaag ttaccaccta tgcggatttc     360
atagacagcc ttaaaacctt tctgactgat atccccttg aatgcaaaaa accagtccaa     420
aaatga                                                                426

<210> SEQ ID NO 5
<211> LENGTH: 558
<212> TYPE: DNA
```

<213> ORGANISM: Homo sapiens

<400> SEQUENCE: 5

```
atgcctcgcc tgttcttgtt ccacctgcta gaattctgtt tactactgaa ccaattttcc    60
agagcagtcg cggccaaatg gaaggacgat gttattaaat tatgcggccg cgaattagtt   120
cgcgcgcaga ttgccatttg cggcatgagc acctggagca aaaggtctct gagccaggaa   180
gatgctcctc agacacctag accagtggca gaaattgtac catccttcat caacaaagat   240
acagaaacta taattatcat gttggaattc attgctaatt tgccaccgga gctgaaggca   300
gccctatctg agaggcaacc atcattacca gagctacagc agtatgtacc tgcattaaag   360
gattccaatc ttagctttga agaatttaag aaacttattc gcaataggca aagtgaagcc   420
gcagacagca atccttcaga attaaaatac ttaggcttgg atactcattc tcaaaaaaag   480
agacgaccct acgtggcact gtttgagaaa tgttgcctaa ttggttgtac caaaaggtct   540
cttgctaaat attgctga                                                 558
```

<210> SEQ ID NO 6
<211> LENGTH: 441
<212> TYPE: DNA
<213> ORGANISM: Mus musculus

<400> SEQUENCE: 6

```
atgaactttc tgctctcttg ggtgcactgg accctggctt tactgctgta cctccaccat    60
gccaagtggt cccaggctgc acccacgaca gaaggagagc agaagtccca tgaagtgatc   120
aagttcatgg atgtctacca gcgaagctac tgccgtccga ttgagaccct ggtggacatc   180
ttccaggagt accccgacga gatagagtac atcttcaagc cgtcctgtgt gccgctgatg   240
cgctgtgcag gctgctgtaa cgatgaagcc ctggagtgcg tgcccacgtc agagagcaac   300
atcaccatgc agatcatgcg gatcaaacct caccaaagcc agcacatagg agagatgagc   360
ttcctacagc acagcagatg tgaatgcaga ccaaagaaag acagaacaaa gccagaaaaa   420
tgtgacaagc caaggcggtg a                                             441
```

<210> SEQ ID NO 7
<211> LENGTH: 576
<212> TYPE: DNA
<213> ORGANISM: Homo sapiens

<400> SEQUENCE: 7

```
atgaactttc tgctgtcttg ggtgcattgg agccttgcct tgctgctcta cctccaccat    60
gccaagtggt cccaggctgc acccatggca gaaggagggg ggcagaatca tcacgaagtg   120
gtgaagttca tggatgtcta tcagcgcagc tactgccatc caatcgagac cctggtggac   180
atcttccagg agtaccctga tgagatcgag tacatcttca gccatcctg tgtgccctg    240
atgcgatgcg ggggctgctg caatgacgag ggcctggagt gtgtgcccac tgaggagtcc   300
aacatcacca tgcagattat gcggatcaaa cctcaccaag ccagcacat aggagagatg    360
agcttcctac agcacaacaa atgtgaatgc agaccaaaga agatagagc aagacaagaa    420
aatccctgtg gccttgctc agagcggaga aagcatttgt ttgtacaaga tccgcagacg   480
tgtaaatgtt cctgcaaaaa cacagactcg cgttgcaagg cgaggcagct tgagttaaac   540
gaacgtactt gcagatgtga caagccgagg cggtga                             576
```

<210> SEQ ID NO 8
<211> LENGTH: 71

```
<212> TYPE: DNA
<213> ORGANISM: Artificial
<220> FEATURE:
<223> OTHER INFORMATION: shVEGF sense_murine

<400> SEQUENCE: 8
gatcccggaa ggagagcaga agtcccatgt tcaagagaca tgggacttct gctctccttt      60 tttttttggaa a                                                          71

<210> SEQ ID NO 9
<211> LENGTH: 71
<212> TYPE: DNA
<213> ORGANISM: Artificial
<220> FEATURE:
<223> OTHER INFORMATION: shVEGF antisense_murine

<400> SEQUENCE: 9
tttccaaaaa aaaaggagag cagaagtccc atgtctcttg aacatgggac ttctgctctc      60
cttccgggat c                                                           71

<210> SEQ ID NO 10
<211> LENGTH: 759
<212> TYPE: DNA
<213> ORGANISM: Homo sapiens

<400> SEQUENCE: 10
atgtggcccc ctgggtcagc ctcccagcca ccgccctcac ctgccgcggc cacaggtctg      60
catccagcgg ctcgccctgt gtccctgcag tgcggctca gcatgtgtcc agcgcgcagc     120
ctcctccttg tggctaccct ggtcctcctg gaccacctca gtttggccag aaacctcccc    180
gtggccactc cagacccagg aatgttccca tgccttcacc actcccaaaa cctgctgagg    240
gccgtcagca acatgctcca gaaggccaga caaactctag aattttaccc ttgcactcct    300
gaagagattg atcatgaaga tatcacaaaa gataaaacca gcacagtgga ggcctgtttta   360 ccattggaat taaccaagaa tgagagttgc ctaaattcca gagagacctc tttcataact    420
aatgggagtt gcctggcctc agaaagacc tcttttatga tggccctgtg ccttagtagt    480
atttatgaag acttgaagat gtaccaggtg gagttcaaga ccatgaatgc aaagcttctg    540
atggatccta agaggcagat cttttctagat caaaacatgc tggcagttat tgatgagctg    600
atgcaggccc tgaatttcaa cagtgagact gtgccacaaa aatcctccct tgaagaaccg    660 gattttttata aaactaaaat caagctctgc atacttcttc atgctttcag aattcgggca    720
gtgactattg atagagtgat gagctatctg aatgcttcc                             759

<210> SEQ ID NO 11
<211> LENGTH: 762
<212> TYPE: DNA
<213> ORGANISM: Homo sapiens

<400> SEQUENCE: 11
atgtggcccc ctgggtcagc ctcccagcca ccgccctcac ctgccgcggc cacaggtctg      60
catccagcgg ctcgccctgt gtccctgcag tgcggctca gcatgtgtcc agcgcgcagc     120
ctcctccttg tggctaccct ggtcctcctg gaccacctca gtttggccag aaacctcccc    180
gtggccactc cagacccagg aatgttccca tgccttcacc actcccaaaa cctgctgagg    240
gccgtcagca acatgctcca gaaggccaga caaactctag aattttaccc ttgcacttct    300
gaagagattg atcatgaaga tatcacaaaa gataaaacca gcacagtgga ggcctgtttta   360
```

| | |
|---|---|
| ccattggaat taaccaagaa tgagagttgc ctaaattcca gagagacctc tttcataact | 420 |
| aatgggagtt gcctggcctc cagaaagacc tcttttatga tggccctgtg ccttagtagt | 480 |
| atttatgaag acttgaagat gtaccaggtg gagttcaaga ccatgaatgc aaagcttctg | 540 |
| atggatccta gaggcagat cttttctagat caaaacatgc tggcagttat tgatgagctg | 600 |
| atgcaggccc tgaatttcaa cagtgagact gtgccacaaa atcctccct tgaagaaccg | 660 |
| gattttata aaactaaaat caagctctgc atacttcttc atgctttcag aattcgggca | 720 |
| gtgactattg atagagtgat gagctatctg aatgcttcct aa | 762 |

```
<210> SEQ ID NO 12
<211> LENGTH: 921
<212> TYPE: DNA
<213> ORGANISM: Homo sapiens

<400> SEQUENCE: 12
```

| | |
|---|---|
| atatgggaac tgaagaaaga tgtttatgtc gtagaattgg attggtatcc ggatgcccct | 60 |
| ggagaaatgg tggtcctcac ctgtgacacc cctgaagaag atggtatcac ctggaccttg | 120 |
| gaccagagca gtgaggtctt aggctctggc aaaaccctga ccatccaagt caaagagttt | 180 |
| ggagatgctg gccagtacac ctgtcacaaa ggaggcgagt tctaagcca ttcgctcctg | 240 |
| ctgcttcaca aaaggaaga tggaatttgg tccactgata ttttaaagga ccagaaagaa | 300 |
| cccaaaaata gacctttct aagatgcgag gccaagaatt attctggacg tttcacctgc | 360 |
| tggtggctga cgacaatcag tactgatttg acattcagtg tcaaaagcag cagaggctct | 420 |
| tctgaccccc aaggggtgac gtgcggagct gctacactct ctgcagagag agtcagaggg | 480 |
| gacaacaagg agtatgagta ctcagtggag tgccaggagg acagtgcctg cccagctgct | 540 |
| gaggagagtc tgcccattga ggtcatggtg gatgccgttc acaagctcaa gtatgaaaac | 600 |
| tacaccagca gcttcttcat cagggacatc atcaaacctg acccacccaa gaacttgcag | 660 |
| ctgaagccat taaagaattc tcggcaggtg gaggtcagct gggagtaccc tgacacctgg | 720 |
| agtactccac attcctactt ctccctgaca ttctgcgttc aggtccaggg caagagcaag | 780 |
| agagaaaaga agatagagt cttcacggac aagacctcag ccacggtcat ctgccgcaaa | 840 |
| aatgccagca ttagcgtgcg ggcccaggac cgctactata gctcatcttg gagcgaatgg | 900 |
| gcatctgtgc cctgcagtta g | 921 |

```
<210> SEQ ID NO 13
<211> LENGTH: 987
<212> TYPE: DNA
<213> ORGANISM: Homo sapiens

<400> SEQUENCE: 13
```

| | |
|---|---|
| atgtgtcacc agcagttggt catctcttgg ttttccctgg ttttctggc atctcccctc | 60 |
| gtggccatat gggaactgaa gaaagatgtt tatgtcgtag aattggattg gtatccggat | 120 |
| gccctggag aaatggtggt cctcacctgt gacacccctg aagaagatgg tatcacctgg | 180 |
| accttggacc agagcagtga ggtcttaggc tctggcaaaa ccctgaccat ccaagtcaaa | 240 |
| gagtttggag atgctggcca gtacacctgt cacaaggag gcgaggttct aagccattcg | 300 |
| ctcctgctgc ttcacaaaaa ggaagatgga atttggtcca ctgatatttt aaaggaccag | 360 |
| aaagaaccca aaaataagac ctttctaaga tgcgaggcca agaattattc tggacgtttc | 420 |
| acctgctggt ggctgacgac aatcagtact gatttgacat tcagtgtcaa agcagcaga | 480 |
| ggctcttctg accccaagg ggtgacgtgc ggagctgcta cactctctgc agagagagtc | 540 |

```
agaggggaca acaaggagta tgagtactca gtggagtgcc aggaggacag tgcctgccca    600
gctgctgagg agagtctgcc cattgaggtc atggtggatg ccgttcacaa gctcaagtat    660
gaaaactaca ccagcagctt cttcatcagg gacatcatca aacctgaccc acccaagaac    720
ttgcagctga agccattaaa gaattctcgg caggtggagg tcagctggga gtaccctgac    780
acctggagta ctccacattc ctacttctcc ctgacattct gcgttcaggt ccagggcaag    840
agcaagagag aaaagaaaga tagagtcttc acggacaaga cctcagccac ggtcatctgc    900
cgcaaaaatg ccagcattag cgtgcgggcc caggaccgct actatagctc atcttggagc    960
gaatgggcat ctgtgccctg cagttag                                        987

<210> SEQ ID NO 14
<211> LENGTH: 45
<212> TYPE: DNA
<213> ORGANISM: Artificial
<220> FEATURE:
<223> OTHER INFORMATION: linker for IL-12

<400> SEQUENCE: 14
ggtggcggtg gctcgggcgg tggtgggtcg ggtggcggcg gatct                     45

<210> SEQ ID NO 15
<211> LENGTH: 574
<212> TYPE: DNA
<213> ORGANISM: Artificial
<220> FEATURE:
<223> OTHER INFORMATION: IRES

<400> SEQUENCE: 15
cccctctccc tccccccccc ctaacgttac tggccgaagc cgcttggaat aaggccggtg     60
tgcgtttgtc tatatgttat tttccaccat attgccgtct tttggcaatg tgagggcccg    120
gaaacctggc cctgtcttct tgacgagcat tcctaggggt cttttcccctc tcgccaaagg   180 aatgcaaggt ctgttgaatg tcgtgaagga agcagttcct ctggaagctt cttgaagaca    240 acaacgtct gtagcgaccc tttgcaggca gcggaacccc ccacctgcg acaggtgcct      300 ctgcggccaa aagccacgtg tataagatac acctgcaaag gcggcacaac cccagtgcca    360
cgttgtgagt tggatagttg tggaaagagt caaatggctc tcctcaagcg tattcaacaa    420
ggggctgaag gatgcccaga aggtaccccca ttgtatggga tctgatctgg ggcctcggtg   480
cacatgcttt acatgtgttt agtcgaggtt aaaaaaacgt ctaggccccc cgaaccacgg    540
ggacgtggtt ttcctttgaa aaacacgatg ataa                                574

<210> SEQ ID NO 16
<211> LENGTH: 1725
<212> TYPE: DNA
<213> ORGANISM: Homo sapiens

<400> SEQUENCE: 16
atgtggcccc ctgggtcagc ctcccagcca ccgccctcac ctgccgcggc cacaggtctg     60
catccagcgg ctcgcccgt gtccctgcag tgccggctca gcatgtgtcc agcgcgcagc    120
ctcctccttg tggctaccct ggtcctcctg gaccacctca gtttggccag aaacctcccc    180
gtggccactc cagacccagg aatgttccca tgccttcacc actcccaaaa cctgctgagg    240
gccgtcagca acatgctcca gaaggccaga caaactctag aatttttaccc ttgcacttct    300 gaagagattg atcatgtaga tatcacaaaa gataaaacca gcagtggga ggcctgtttta    360
```

```
ccattggaat taaccaagaa tgagagttgc ctaaattcca gagagacctc tttcataact    420
aatgggagtt gcctggcctc cagaaagacc tcttttatga tggccctgtg ccttagtagt    480
atttatgaag acttgaagat gtaccaggtg gagttcaaga ccatgaatgc aaagcttctg    540
atggatccta agaggcagat cttcctagat caaaacatgc tggcagttat tgatgagctg    600
atgcaggccc tgaatttcaa cagtgagact gtgccacaaa atcctccct tgaagaaccg     660 gatttttata aaactaaaat caagctctgc atacttcttc atgctttcag aattcgggca    720
gtgactattg atagagtgat gagctatctg aatgcttccg gtggcggtgg ctcgggcggt    780
ggtgggtcgg gtggcggcgg atctatatgg gaactgaaga agatgtttta tgtcgtagaa    840
ttggattggt atccggatgc ccctggagaa atggtggtcc tcacctgtga caccctgaa     900 gaagatggta tcacctggac cttgaccag  agcagtgagg tcttaggctc tggcaaaacc    960
ctgaccatcc gagtcaaaga gtttggagat gctggccagt acacctgtca aaaggaggc    1020 gaggttctaa gccattcgct cctgctgctt cacaaaaagg aagatggaat ttggtccact   1080
gatattttaa aggaccagaa agaacccaaa ataagacctt tctaagatg cgaggccaag   1140 aattattctg gacgtttcac ctgctggtgg ctgacgacaa tcagtactga tttgacattc   1200
agtgtcaaaa gcagcagagg ctcttctgac ccccaagggg tgacgtgcgg agctgctaca   1260
ctctctgcag agagtcag agggggacaac aaggagtatg agtactcagt ggagtgccag    1320
gaggacagtg cctgcccagc tgctgaggag agtctgccca ttgaggtcat ggtggatgcc   1380
gttcacaagc tcaagtatga aaactacacc agcagcttct tcatcaggga catcatcaaa   1440
cctgacccac ccaagaactt gcagctgaag ccattaaaga attctcggca ggtggaggtc   1500
agctgggagt accctgacac ctggagtact ccacattcct acttctccct gacattctgc   1560
gttcaggtcc agggcaagag caagagagaa agaaagata gagtcttcac ggacaagacc   1620
tcagccacgg tcatctgccg caaaaatgcc agcattagcg tgcgggccca ggaccgctac   1680
tatagctcat cttggagcga atgggcatct gtgccctgca gttag                   1725
```

<210> SEQ ID NO 17
<211> LENGTH: 2331
<212> TYPE: DNA
<213> ORGANISM: Homo sapiens

<400> SEQUENCE: 17

```
atgtggcccc tgggtcagc ctcccagcca ccgccctcac ctgccgcggc cacaggtctg     60
catccagcgg ctcgccctgt gtccctgcag tgccggctca gcatgtgtcc agcgcgcagc   120
ctcctccttg tggctaccct ggtcctcctg gaccacctca gtttggccag aaacctcccc   180
gtggccactc cagacccagg aatgttccca tgccttcacc actcccaaaa cctgctgagg   240
gccgtcagca acatgctcca gaaggccaga caaactctag aattttaccc ttgcacttct   300
gaagagattg atcatgaaga tatcacaaaa gataaaacca gcacagtgga ggcctgttta   360
ccattggaat taaccaagaa tgagagttgc ctaaattcca gagagacctc tttcataact    420
aatgggagtt gcctggcctc cagaaagacc tcttttatga tggccctgtg ccttagtagt    480
atttatgaag acttgaagat gtaccaggtg gagttcaaga ccatgaatgc aaagcttctg    540
atggatccta agaggcagat cttcctagat caaaacatgc tggcagttat tgatgagctg    600
atgcaggccc tgaatttcaa cagtgagact gtgccacaaa atcctccct  tgaagaaccg    660 gatttttata aaactaaaat caagctctgc atacttcttc atgctttcag aattcgggca    720
gtgactattg atagagtgat gagctatctg aatgcttcct aagccccccc ccctaacgtt    780
```

```
actggccgaa gccgcttgga ataaggccgg tgtgcgtttg tctatatgtt attttccacc      840
atattgccgt cttttggcaa tgtgagggcc cggaaacctg ccctgtctt cttgacgagc       900 attcctagct aggggtcttt ccctctcgc caaaggaatg caaggtctgt tgaatgtcgt       960
gaaggaagca gttcctctgg aagcttcttg aagacaaaca cgtctgtag cgacccttg      1020 caggcagcgg aaccccccac ctggcgacag gtgcctctgc ggccaaaagc cacgtgtata    1080
agatacacct gcaaaggcgg cacaaccca gtgccacgtt gtgagttgga tagttgtgga     1140
aagagtcaaa tggctctcct caagcgtatt caacaagggg ctgaaggatg cccagaaggt    1200
accccattgt atgggatctg atctggggcc tcggtgcaca tgctttacat gtgtttagtc    1260
gaggttaaaa aaacgtctag gccccccgaa ccacgggac gtggttttcc tttgaaaaac     1320
acgatgataa tatggccaca accaatgtgt caccagcagt tggtcatctc ttggttttcc    1380
ctggtttttc tggcatctcc cctcgtggcc atatgggaac tgaagaaaga tgtttatgtc    1440
gtagaattgg attggtatcc ggatgcccct ggagaaatgg tggtcctcac ctgtgacacc    1500
cctgaagaag atggtatcac ctggaccttg gaccagagca gtgaggtctt aggctctggc    1560
aaaaccctga ccatccaagt caaagagttt ggagatgctg ccagtacac ctgtcacaaa     1620 ggaggcgagg ttctaagcca ttcgctcctg ctgcttcaca aaaaggaaga tggaatttgg   1680
tccactgata ttttaaagga ccagaaagaa cccaaaaata agaccttct aagatgcgag    1740 gccaagaatt attctggacg tttcacctgc tggtggctga cgacaatcag tactgatttg    1800
acattcagtg tcaaaagcag cagaggctct tctgaccccc aagggtgac gtgcggagct     1860 gctacactct ctgcagagag agtcagaggg gacaacaagg agtatgagta ctcagtggag    1920
tgccaggagg acagtgcctg cccagctgct gaggagagtc tgcccattga ggtcatggtg    1980
gatgccgttc acaagctcaa gtatgaaaac tacaccagca gcttcttcat cagggacatc    2040
atcaaacctg acccacccaa gaacttgcag ctgaagccat taagaattc tcggcaggtg    2100 gaggtcagct gggagtaccc tgacacctgg agtactccac attcctactt ctccctgaca    2160
ttctgcgttc aggtccaggg caagagcaag agagaaaaga agatagagt cttcacggac    2220 aagacctcag ccacggtcat ctgccgcaaa aatgccagca ttagcgtgcg ggcccaggac    2280
cgctactata gctcatcttg gagcgaatgg gcatctgtgc cctgcagtta g             2331
```

<210> SEQ ID NO 18
<211> LENGTH: 789
<212> TYPE: DNA
<213> ORGANISM: Homo sapiens

<400> SEQUENCE: 18

```
acacagagag aaaggctaaa gttctctgga ggatgtggct gcagagcctg ctgctcttgg       60
gcactgtggc ctgcagcatc tctgcacccg cccgctcgcc cagccccagc acgcagccct      120
gggagcatgt gaatgccatc caggaggccc ggcgtctcct gaacctgagt agagacactg      180
ctgctgagat gaatgaaaca gtagaagtca tctcagaaat gtttgacctc caggagccga      240
cctgcctaca gaccccgctg gagctgtaca agcagggcct gcgggcagc ctcaccaagc       300 tcaagggccc cttgaccatg atggccagcc actacaagca gcactgccct ccaaccccgg      360
aaacttcctg tgcaacccag attatcacct ttgaaagttt caaagagaac ctgaaggact      420
ttctgcttgt catccccttt gactgctggg agccagtcca ggagtgagac cggccagatg     480
aggctggcca agccggggag ctgctctctc atgaaacaag agctagaaac tcaggatggt    540
```

-continued

```
catcttggag ggaccaaggg gtgggccaca gccatggtgg gagtggcctg gacctgccct    600
gggcacactg accctgatac aggcatggca gaagaatggg aatattttat actgacagaa    660
atcagtaata tttatatatt tatattttta aaatatttat ttatttattt atttaagttc    720
atattccata tttattcaag atgttttacc gtaataatta ttattaaaaa tagcttctaa    780
aaaaaaaaa                                                            789
```